US012385876B2

(12) United States Patent
Rogers et al.

(10) Patent No.: US 12,385,876 B2
(45) Date of Patent: Aug. 12, 2025

(54) METHODS OF OPERATING AND CALIBRATING A GAS SENSOR, AND RELATED GAS SENSORS

(71) Applicant: Nevada Nanotech Systems Inc., Sparks, NV (US)

(72) Inventors: Benjamin S. Rogers, Reno, NV (US); Ralph G. Whitten, Reno, NV (US); Vaughn N. Hartung, Reno, NV (US); Onnik Yaglioglu, Thousand Oaks, CA (US); Jesse D. Adams, Reno, NV (US)

(73) Assignee: Nevada Nanotech Systems Inc., Sparks, NV (US)

( * ) Notice: Subject to any disclaimer, the term of this patent is extended or adjusted under 35 U.S.C. 154(b) by 315 days.

(21) Appl. No.: 17/755,057

(22) PCT Filed: Oct. 22, 2020

(86) PCT No.: PCT/US2020/070681
§ 371 (c)(1),
(2) Date: Apr. 20, 2022

(87) PCT Pub. No.: WO2021/081553
PCT Pub. Date: Apr. 29, 2021

(65) Prior Publication Data
US 2022/0381731 A1 Dec. 1, 2022

Related U.S. Application Data

(60) Provisional application No. 62/924,576, filed on Oct. 22, 2019.

(51) Int. Cl.
*G01N 27/416* (2006.01)
*G01N 27/12* (2006.01)
*G01N 27/18* (2006.01)

(52) U.S. Cl.
CPC ....... *G01N 27/4163* (2013.01); *G01N 27/121* (2013.01); *G01N 27/18* (2013.01)

(58) Field of Classification Search
CPC ... G01N 27/4163; G01N 27/121; G01N 27/18
See application file for complete search history.

(56) References Cited

U.S. PATENT DOCUMENTS 5,418,131 A    5/1995 Butts
5,716,506 A    2/1998 Maclay et al.
(Continued)

FOREIGN PATENT DOCUMENTS

CN    103328954    9/2013
CN    106662559    5/2017
(Continued)

OTHER PUBLICATIONS

English translation of JP2004286492 accessed from iq.ip.com.*
(Continued)

*Primary Examiner* — Kristina M Deherrera
*Assistant Examiner* — Jean F Morello
(74) *Attorney, Agent, or Firm* — RAY QUINNEY & NEBEKER; Daniel J. Bezdjian

(57) ABSTRACT

A method of calibrating a gas sensor comprises determining a sensitivity of a gas sensor to one or more conditions proximate the gas sensor, determining one or more initial calibration factors comprising a sensitivity of the gas sensor to one or more analytes of interest, determining a current sensitivity of the gas sensor to the one or more conditions proximate the gas sensor by measuring a response of the gas sensor while the one or more conditions proximate the gas sensor varies during operation of the gas sensor, and adjusting the one or more initial calibration factors of the gas sensor based, at least in part on the current sensitivity of the gas sensor to the one or more conditions proximate the gas
(Continued)

sensor, and a relationship between the sensitivity of the gas sensor to the one or more analytes of interest to the sensitivity of the gas sensor to the one or more conditions proximate the gas sensor. Related gas detectors, related methods of compensating and calibrating the gas sensors, and methods of determining a functionality of the gas sensors are disclosed.

19 Claims, 8 Drawing Sheets

(56) References Cited

U.S. PATENT DOCUMENTS

| | | | |
|---|---|---|---|
| 6,132,083 A * | 10/2000 | Enala | G01N 25/18 374/44 |
| 6,237,394 B1 | 5/2001 | Harris et al. | |
| 9,523,665 B2 | 12/2016 | Fleischer et al. | |
| 10,317,357 B2 * | 6/2019 | Le Neel | H01L 25/50 |
| 10,724,976 B2 | 7/2020 | Rogers et al. | |
| 2003/0019275 A1 | 1/2003 | Lloyd et al. | |
| 2007/0017276 A1 * | 1/2007 | Trutna | G01N 27/223 73/29.01 |
| 2008/0156071 A1 * | 7/2008 | Tobias | G01N 33/0006 73/23.31 |
| 2009/0188297 A1 | 7/2009 | Willett et al. | |
| 2012/0073357 A1 * | 3/2012 | Gatzmanga | G01N 27/18 73/25.03 |
| 2013/0301052 A1 | 11/2013 | Macgregor et al. | |
| 2016/0077071 A1 | 3/2016 | Chancey | |
| 2018/0052124 A1 | 2/2018 | Rogers et al. | |

FOREIGN PATENT DOCUMENTS

| | | |
|---|---|---|
| CN | 107771056 | 3/2018 |
| CN | 109716116 | 5/2019 |
| JP | 2003-185613 | 3/2003 |
| JP | 2004286492 A * | 10/2004 |
| KR | 10-2009-0056731 A | 6/2009 |
| WO | 2009/019467 A1 | 2/2009 |
| WO | 2012/059743 | 10/2012 |
| WO | 2014/193936 A1 | 12/2014 |
| WO | 2018/034948 | 2/2018 |

OTHER PUBLICATIONS

International Search Report from International Application No. PCT/US2020/070681, mailed Feb. 2, 2021, 3 pages.
International Written Opinion from International Application No. PCT/US2020/070681, mailed Feb. 2, 2021, 6 pages.
Chinese First Office Opinion Notice and Search Report for Chinese Application No. CN109716116, dated Apr. 17, 2024, 16 pages with English translation.
Supplementary European Search Report ("European Patent Office") for European Application No. EP 20 87 8723, dated Oct. 20, 2023, 7 pages.
JP2022-523321, May 29, 2023, Notification of Reasons for Refusal.
Canadian Examiner's Report ("Canadian Intellectual Property Office") for Canadian Application No. 3,153,895, dated Jan. 5, 2024, 4 pages.
Chinese Second Office Action for Chinese Application No. 202080073802.9, dated Nov. 9, 2024, 15 pages with English translation.
Notice of Reasons for Rejection for Korean Application No. 10-2022-7016905, mailed Nov. 7, 2024 (22 pages).
Chinese Rejection Decision for Chinese Application No. 202080073802.9, dated Mar. 19, 2025 (14 pp.).

* cited by examiner

METHODS OF OPERATING AND CALIBRATING A GAS SENSOR, AND RELATED GAS SENSORS

CROSS-REFERENCE TO RELATED APPLICATIONS

This application is a national phase entry under 35 U.S.C. § 371 of International Patent Application PCT/US2020/070681, filed Oct. 22, 2020, designating the United States of America and published as International Patent Publication WO 2021/081553 A1 on Apr. 29, 2021, which claims the benefit under Article 8 of the Patent Cooperation Treaty to U.S. Patent Application Ser. No. 62/924,576, filed Oct. 22, 2019.

TECHNICAL FIELD

Embodiments of the disclosure relate generally to methods of calibrating and compensating a sensor during normal use and operation based on one or more conditions (e.g., one or more of a concentration of water vapor (humidity), temperature, pressure, a concentration of one or more gases proximate the sensor) proximate the sensor, and to related sensors. More particularly, embodiments of the disclosure relate to methods of calibrating and compensating a sensor based on a relationship between a sensitivity of the sensor to the one or more conditions (e.g., water concentration) and a sensitivity of the sensor to at least one analyte of interest, the sensitivity of the sensor to the one or more conditions (e.g., water concentration) determined during use and operation of the sensor based on the one or more conditions (e.g., a concentration of water) proximate the sensor.

BACKGROUND

Gas sensors conventionally include one or more coatings formulated and configured to interact with an analyte of interest responsive to exposure to a sample comprising the analyte of interest. For example, a metal oxide semiconductor (MOS) sensor may include an exposed metal oxide coating formulated and configured to interact with an analyte of interest. Responsive to interaction of the metal oxide coating with the analyte of interest, an electrical resistance of the metal oxide coating may change due to the interaction of the metal oxide coating with the analyte of interest. The concentration or the presence of the analyte of interest is determined based on the change in electrical resistance of the metal oxide coating relative to the electrical resistance of the metal oxide coating when exposed to, for example, a reference gas or the ambient environment. A resonant sensor, such as a microcantilever sensor, may have coatings such as oxides or polymers with absorptive characteristics that may change over time (e.g., due to poisoning or fouling of the coating). These changes affect the sensitivity of the resonant sensors to changes in concentration of the analyte.

Over the life of the gas sensor, the gas sensor may be exposed to various gases at various conditions, as well as swings in temperature, pressure, humidity, or concentration of one or more gases. The objective of many gas sensors is to accurately report the concentration of gases present proximate the gas sensor. Ambient conditions, such as temperature, pressure, and humidity, proximate the gas sensor may affect the accuracy of the readings of the gas sensor. Humidity is of particular concern since the water content can range from less than 1 ppm to several thousand ppm in the air and many gas sensors are cross sensitive to water vapor. Thus, the concentration of water vapor proximate the gas sensor can affect the output of the gas sensor, independent of the concentration of analytes of interest proximate the gas sensor. Additionally, as the gas sensor ages, it may exhibit a different sensitivity to exposure to the analyte of interest. In other words, the response of the gas sensor (e.g., including a metal oxide coating or an electrochemical coating) to exposure to the same concentration of the analyte of interest may exhibit a different resistance over the life of the gas sensor. Alternatively, a sensitivity of a resonant frequency sensor to a concentration of an analyte may change over the life of the resonant sensor. In addition, the metal oxide coating may become poisoned as it reacts and interacts with different gases in the environment. Furthermore over time, the sensor response may drift, in so-called "sensor drift," wherein the output of the sensor changes slowly (i.e., drifts) independently of the measured property (e.g., the concentration of the analyte of interest in a gas sample). Time, sensor drift, aging, chemical history, and poisoning of the gas sensor may reduce an accuracy of the gas sensor such that the response of the gas sensor is not representative of the actual concentration of the analyte present in the sample proximate the gas sensor. Sensor drift may result in false alarms, inaccuracy, or may result in a lack of detection of the analyte of interest when the analyte of interest is present proximate the gas sensor.

BRIEF SUMMARY

Embodiments disclosed herein include methods of calibrating a gas sensor and to related gas sensors. For example, in accordance with one embodiment, a method of determining at least one property of a gas comprises determining a sensitivity of a gas sensor to humidity, adjusting at least one stored calibration parameter of the gas sensor to at least one analyte of interest using a predetermined relationship between the sensitivity of the gas sensor to humidity and a sensitivity of the gas sensor to the at least one analyte of interest to determine an adjusted calibration parameter, and compensating an output of the gas sensor by the adjusted calibration parameter.

In additional embodiments, a method of calibrating a gas sensor comprises exposing a gas sensor to water vapor having at least one of a known concentration or a measured concentration; measuring a response of the gas sensor to exposure to a change in humidity concentration, and after measuring a response of the gas sensor to exposure to the humidity, adjusting the calibration factors applied to the response of the gas sensor to exposure to an analyte of interest based on the response of the gas sensor to exposure to the humidity.

In further embodiments, a gas detector comprises a housing, a gas sensor configured to be exposed to a sample gas located proximate the gas detector, at least one environmental sensor configured to determine a humidity concentration proximate the gas sensor, and a processor configured to determine a sensitivity of the gas sensor to exposure to humidity based on the output of the gas sensor responsive to exposure to samples having different humidity concentrations, and calibrating the response of the gas sensor based on a relationship between the sensitivity of the gas sensor to exposure to humidity and a sensitivity of the gas sensor to exposure to at least one analyte of interest. In a similar fashion, temperature and atmospheric pressure sensor sensitivity may be incorporated into the calibration to further enhance the accuracy of the sensor. In a multi-sensor system, a sensor can be calibrated by other sensors in the system based on exposure to any environmental condition that illicit(s) a response on two or more sensors; for example, any two sensors that are cross sensitive to changes in temperature, pressure, humidity, CO, $CO_2$ or any number of volatile organic compounds may be cross correlated to derive compensation and calibration factors.

In yet additional embodiments, a method of calibrating a gas sensor comprises determining a sensitivity of a gas sensor to one or more conditions proximate the gas sensor, determining one or more initial calibration factors comprising a sensitivity of the gas sensor to one or more analytes of interest, determining a current sensitivity of the gas sensor to the one or more conditions proximate the gas sensor by measuring a response of the gas sensor while the one or more conditions proximate the gas sensor varies during operation of the gas sensor, and adjusting the one or more initial calibration factors of the gas sensor based, at least in part on the current sensitivity of the gas sensor to the one or more conditions proximate the gas sensor, and a relationship between the sensitivity of the gas sensor to the one or more analytes of interest to the sensitivity of the gas sensor to the one or more conditions proximate the gas sensor.

In further embodiments, a method of operating a gas sensor configured to detect at least one analyte of interest comprises determining at least one of a humidity compensation factor, a temperature compensation factor, and a pressure compensation factor by measuring a response of the sensor at one or more of a plurality of humidity levels, a plurality of temperatures, and a plurality of pressures in the absence of at least one analyte of interest, compensating a response of the gas sensor for effects of one or more of humidity, temperature, and pressure based on the at least one of the humidity compensation factor, the temperature compensation factor, and the pressure compensation factor and a current one or more of the humidity, temperature, and pressure proximate the sensor to determine a compensated response of the gas sensor, and calibrating the compensated response of the gas sensor based, at least in part, on a relationship between a sensitivity of the gas sensor to the at least one analyte of interest and a sensitivity of the gas sensor to the one or more of humidity, temperature, and pressure.

In additional embodiments, a gas detector comprises a gas sensor configured to be exposed to one or more gases located proximate the gas sensor, at least one environmental sensor configured to determine at least one of humidity, temperature, and pressure proximate the gas sensor, and a processing subsystem. The processing subsystem is configured to determine a sensitivity of the gas sensor to one or more conditions proximate the gas sensor based on a relationship between an output of the gas sensor and the one or more conditions proximate the gas sensor, and calibrate the output of the gas sensor based on a relationship between the sensitivity of the gas sensor to the one or more conditions proximate the gas sensor and a sensitivity of the gas sensor to exposure to one or more gases of interest.

In further embodiments, a method of determining a functionality of a gas sensor comprises measuring a condition proximate a gas sensor with a sensor while measuring a response of the gas sensor, and based on and the measured condition proximate the gas sensor and a response of the gas sensor at varying conditions proximate the gas sensor, determining a functionality of the gas sensor.

DETAILED DESCRIPTION

Figure 1:
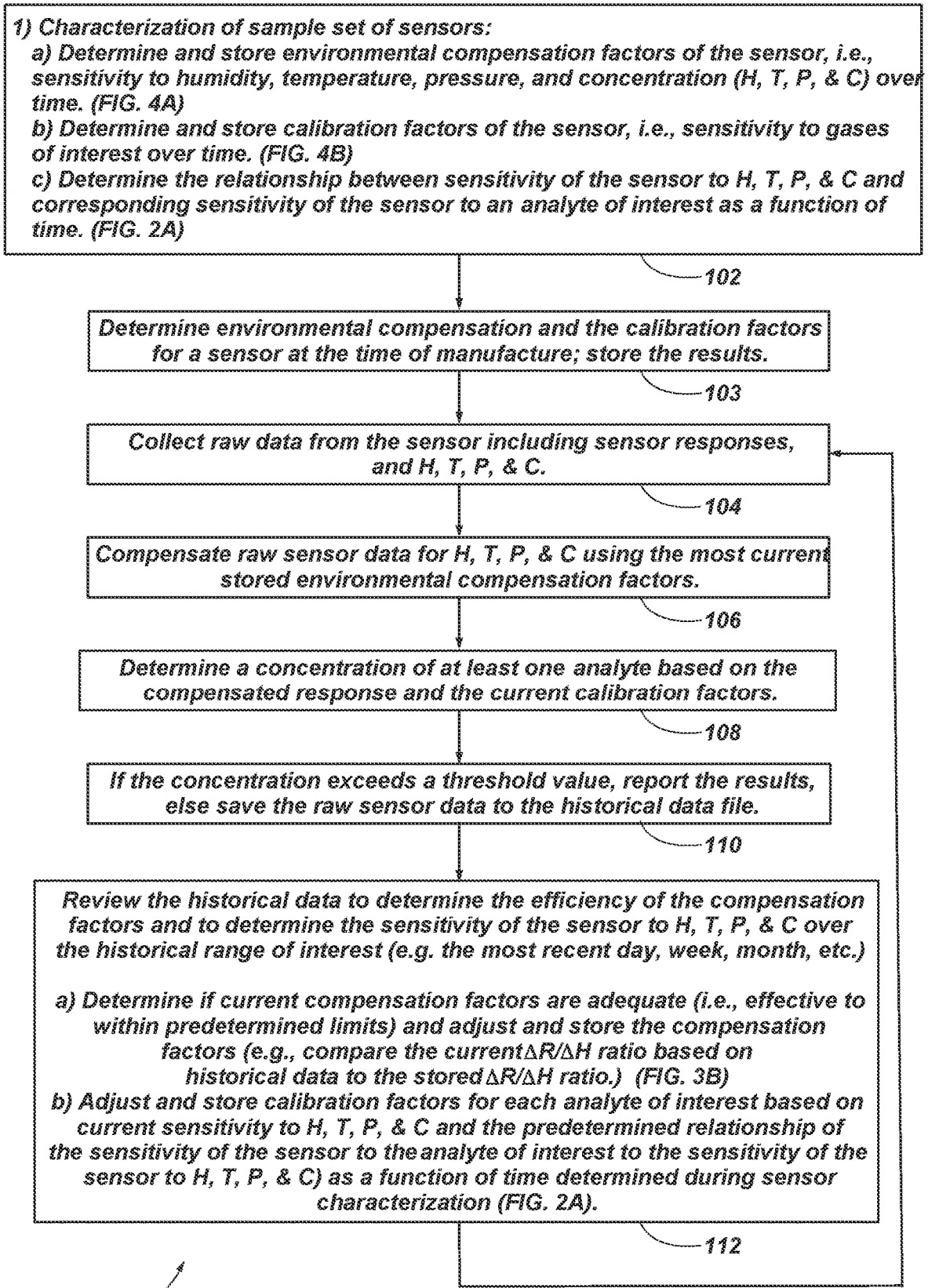
FIG. 1 is a simplified flow diagram of a method of measuring at least one property of an analyte of interest with a sensor, in accordance with embodiments of the disclosure.

Illustrations presented herein are not meant to be actual views of any particular material, component, or system, but are merely idealized representations that are employed to describe embodiments of the disclosure.

The following description provides specific details, such as material types, material thicknesses, and processing techniques in order to provide a thorough description of embodiments described herein. However, a person of ordinary skill in the art will understand that the embodiments disclosed herein may be practiced without employing these specific details. Indeed, the embodiments may be practiced in conjunction with conventional fabrication techniques employed in the industry.

According to embodiments described herein, a method of calibrating and compensating a sensor (e.g., a gas sensor, another sensor) during use and operation of the sensor (e.g., in the field) is described. The method includes determining a current (e.g., present) sensitivity of the sensor to a change in water vapor exposure (i.e., a current sensitivity of the sensor to humidity) proximate the sensor. The humidity concentration (i.e., the humidity) proximate the sensor may be determined (e.g., measured) using one or more environmental sensors located proximate to the sensor. The sensitivity of the sensor to exposure to humidity may be determined, such as by correlating the humidity (e.g., water vapor concentration) proximate the sensor to a response of the sensor (e.g., an output signal of the sensor relative to a baseline output signal of the sensor when exposed to a known sample having a known water concentration, which may correlate to a change in the output signal of the sensor). In some embodiments, the sensitivity of the sensor to one or more of the temperature, pressure, humidity, and a concentration of one or more gases other than the at least one analyte of interest, may be determined.

The sensor may be positioned at a location exhibiting natural changes in humidity. For example, air in ambient conditions may exhibit a water vapor concentration ranging from less than about 100 ppm to about 10,000 ppm water vapor. Over the course of a day, the concentration of water vapor in the air may vary by thousands of ppm due to diurnal variations in temperature, pressure, and humidity. In addition, the sensor may be exposed to varying concentrations of one or more gases (e.g., carbon dioxide, carbon monoxide, one or more volatile organic compounds (VOCs)) (e.g., compounds of carbon excluding carbon monoxide, carbon dioxide, carbonic acid, metallic carbides or carbonates, and ammonium carbonate, which precipitate in photochemical reactions). Accordingly, the sensor may be positioned at a location exhibiting diurnal variations in one or more conditions. The one or more conditions exhibiting the diurnal variations may include one or more of humidity (e.g., relative humidity), temperature, pressure, and concentration of one or more gases proximate the sensor. The sensitivity of the sensor to water concentration may be determined based on a relationship between the output of the sensor responsive to exposure to samples from the environment proximate the sensor exhibiting natural variations in humidity and the known or measured humidity proximate the sensor. Accordingly, the sensitivity of the sensor to humidity (i.e., the sensitivity of the sensor to exposure to humidity) may be determined based on a change in the output of the sensor relative to a baseline output of the sensor at each of one or more (e.g., one, two, three, four, ten, twenty, etc.) humidity concentrations. In some embodiments, the sensor may be exposed to a known concentration of water vapor (humidity), such as during factory calibration (e.g., where humidity is a more convenient calibration gas, such as where the analyte is dangerous or explosive). Similarly, the sensor may be exposed to diurnal changes in temperature, pressure, and concentration of one or more gases (other than the at least one analyte of interest).

The sensor may exhibit a predetermined relationship between the sensitivity of the sensor to at least one conditions proximate the sensor and the sensitivity of the sensor to at least one analyte of interest. For example, the sensor may exhibit a predetermined relationship between the sensitivity of the sensor to exposure to humidity and a sensitivity of the sensor to at least one analyte of interest (i.e., a sensitivity of the sensor to exposure to the at least one analyte of interest). The sensor may further exhibit a predetermined relationship between the sensitivity of the sensor to temperature and the sensitivity of the sensor to the at least one analyte of interest; the sensitivity of the sensor to pressure and the sensitivity of the sensor to the at least one analyte of interest; and the sensitivity of the sensor to a concentration of one or more gases (other than the at least one analyte of interest) proximate the sensor and the sensitivity of the sensor to the at least one analyte of interest. The sensor may exhibit a unique relationship between the sensitivity of the sensor to one or more environmental conditions proximate the sensor (e.g., one or more of humidity, temperature, pressure, and concentration of one or more gases) to the sensitivity of the sensor to one or more analytes of interest. In some embodiments, the sensor may exhibit a unique relationship between the sensitivity of the sensor to exposure to each of humidity, temperature, pressure, and the concentration of one or more gases and the sensitivity of the sensor to each analyte of interest. In some embodiments, the relationship may be dependent on the materials used in the sensor and may be determined in a factory, such as when the sensor (or a quantity of similar as sensors) is manufactured. For example, based on the materials selected for the sensor and the operating conditions of the sensor, it may be determined through laboratory testing that a particular sensor has an inherent capability of responding to the at least one analyte of interest that is a predetermined amount, proportion, or larger (or smaller) than the response of the particular sensor to the one or more of humidity, temperature, pressure, and concentration of the one or more gases. If the sensitivity (e.g., response) of the sensor to the one or more of humidity, temperature, pressure, and concentration of the one or more gases changes, a calibration factor (parameter) for the at least one analyte of interest may be adjusted based on the predetermined relationship. The calibration factor may be applied to the response of the sensor to determine an accurate property (e.g., concentration of the at least one analyte of interest) of a sample analyzed by the sensor. Accordingly, the sensitivity of the sensor to the at least one analyte of interest may be determined based on the sensitivity of the sensor to one or more of humidity, temperature, pressure, and the concentration of the one or more gases and the predetermined relationship between the sensitivity of the sensor to the one or more of humidity, temperature, pressure, and the concentration of the one or more gases and the sensitivity of the sensor to the at least one analyte of interest. One or more saved calibration factors (parameters) of the sensor may be adjusted based on the determined sensitivity of the sensor to the at least one analyte of interest. In some embodiments, the sensitivity of the sensor to the one or more of humidity, temperature, pressure, and the concentration of the one or more gases may be determined at predetermined intervals (e.g., seconds, minutes, hours, every six hours, every twelve hours, daily, weekly, biweekly, monthly, annually, etc.) and the sensor may be recalibrated at such intervals. In another embodiment, the predetermined interval may be based on the count of historical data values stored in memory or on the count of the number of measurements taken since the most recent recalibration. The sensor may be recalibrated manually (e.g., based on a user input) in some embodiments. In other embodiments, the sensor may include a processing subsystem configured to recalibrate the sensor responsive to, for example, a change in the sensitivity of the sensor to the one or more conditions proximate the sensor.

As used herein, the terms "water concentration," "humidity concentration," "concentration of water," and "concentration of humidity" are used interchangeably and refer to a concentration (e.g., in ppm) of water vapor.

As used herein, the terms "sensor" and "gas sensor" are used interchangeably.

As used herein, the terms "output" of a sensor, "output signal" of a sensor, and "response" of a sensor are used interchangeably. The output of a sensor may be or may correspond to a resistance of the sensor, such as a resistance of a coating material of the sensor, a resonant frequency of the sensor, a change in the resistance ($\Delta R$) of the sensor, a change in conductance ($\Delta G$) of the sensor, a change in voltage ($\Delta V$) of the sensor, a change in current ($\Delta I$) of the sensor, a change in the resonant frequency ($\Delta F$) of the sensor, or any other sensor output or combinations thereof.

As used herein, the term "baseline response" of a gas sensor means and includes a response of a sensor when exposed to a baseline material (e.g., a baseline gas, such as air) in the absence of analytes of interest and at a baseline humidity, temperature, and pressure.

As used herein, the term "sensitivity" of a sensor to a particular input parameter (e.g., humidity, temperature, pressure, a concentration of one or more gases, at least one analyte of interest) means and includes a change in the output of the sensor per unit change of the particular input parameter being measured. As one example, the sensitivity of a sensor to water concentration (e.g., humidity) means and includes the change in output of the sensor per change in water vapor concentration (e.g., per change in ppm of water vapor, change in mole percent water vapor, change in relative humidity (%) or absolute humidity ($g/m^3$), etc.) to which the sensor is exposed. Similarly, a sensitivity of a sensor to an analyte of interest means and includes the change in output of the sensor per change in concentration of the analyte of interest to which the sensor is exposed. The terms "sensitivity of the sensor to water," "sensitivity of the sensor to exposure to water," and "sensitivity of the sensor to absolute humidity" are used interchangeably. The terms "sensitivity of the sensor to an analyte of interest" and "sensitivity of the sensor to exposure to the analyte of interest" are used interchangeably.

As used herein, the terms "calibration" and "compensation" have distinct meanings. As used herein, the term "compensation" of a sensor means and includes adjustment of a response of a sensor by one or more factors based on environmental conditions proximate the sensor at the time the sensor response is measured, thus providing greater accuracy of the properties determined by the sensor (e.g., gas concentration and/or identification). By way of nonlimiting example, a sensor response may be compensated for one or more of a current temperature, a current pressure, a current humidity, and a current concentration of one or more gases proximate the sensor at the time the sensor response is measured.

As used herein, the term "calibration" of a sensor means and includes correction of a sensor response for changes in the sensitivity of the sensor to one or more analytes of interest. Thus, as used herein "calibration" means and includes adjustment the output of the sensor based on one or more calibration factors and on the current sensitivity of the sensor to one or more of humidity, temperature, pressure, and the concentration of one or more gases (other than the at least one analyte of interest) proximate the sensor and the relationship between the sensitivity of the sensor to the one or more of humidity, temperature, pressure, and the concentration of the one or more gases proximate the sensor and the sensitivity of the sensor to at least one analyte of interest. The sensor output may be calibrated with one or more of an algorithm, one or more calibration factors, a look-up table, or another parameter that is applied to the output of the sensor to obtain a calibrated sensor response to facilitate an improved signal from the sensor based on current conditions (e.g., aging) of the sensor. Calibration of the sensor output may facilitate determination of the concentration of the one or more gases and proper gas identification. The calibration factors (e.g., the calibration algorithm) of a sensor may change over the lifetime of the sensor, such as by sensor drift, aging, chemical exposure history, poisoning, etc.

Compensation of the sensor may include adjusting a baseline response of the sensor. The baseline response of the sensor is the sensor output when no analytes of interest are proximate the sensor (e.g., such as when the sensor is exposed to a baseline gas or to an ambient atmosphere substantially free of (e.g., not including) analytes of interest). The baseline response may change due to variations in temperature, pressure, humidity, and/or concentration of gases (e.g., other than the at least one analyte of interest) proximate the sensor. Stated another way, the baseline response may be affected by the temperature, pressure, humidity, and/or concentration of gases proximate the sensor. A compensated response of a sensor may generally be flat (i.e., exhibit substantially no change), even when the temperature, pressure, relative humidity, and/or concentration of gases proximate the gas sensor are changing. In other words, the response of the sensor may be compensated for changes in humidity, temperature, pressure, and concentration of gases relative to a respective baseline humidity, temperature, pressure, and concentration of gases such that the compensated response of the sensor (compensated for changes in humidity, temperature, pressure, and concentration of gases) remains within a predetermined range (e.g., exhibits less than a predetermined variation). Accordingly, the compensated response of the sensor may be relatively (e.g., substantially) flat when the sensor is not exposed to one or more analytes of interest. A deviation from a flat response of the sensor that correlates in time and duration to a temperature, pressure, humidity, and/or concentration of gases event (i.e., a change in temperature, pressure, humidity, and/or concentration of gases, respectively) may be an indication that the compensation for that particular parameter (temperature, pressure, humidity, or concentration of gases) should be adjusted such that the compensated sensor response is returned to a flat response with respect to changing environmental conditions. Changes in the sensor response (e.g., the compensated response of the sensor) that do not correlate in time and duration to changes in temperature, pressure, relative humidity, and/or concentration of gases proximate the sensor may be an indication that changes proximate the changes to the compensated sensor response are due to changes in conditions other than temperature, pressure, relative humidity, and/or concentration of gases proximate the sensor (such as changes in a concentration of one or more analytes of interest (e.g., a gas different than a baseline or reference gas) proximate the gas sensor). In some such embodiments, the compensation parameters may not be adjusted based on the compensated sensor response when the one or more analytes of interest are present proximate the sensor. In a multi-sensor system, differential responses among various sensors (e.g., a sensor including a coating formulated and configured to interact with an analyte gas and an uncoated sensor or a sensor including an inert coating) may also be used to detect the presence of one or more analytes of interest (e.g., in a gas) proximate the sensor, indicating that compensation factors should not be adjusted based on the response of the sensor to exposure to the one or more analytes.

Initial (e.g., baseline) calibration factors, compensation factors, and the relationship between the response of the sensor to one or more of humidity, temperature, pressure, and the concentration of one or more gases proximate the sensor and the response of the sensor to the at least one analyte may be determined at the time the sensor is manufactured and stored in the memory of the sensor at the factory. In use and operation, temperature, pressure, and humidity may be measured with an environmental sensor proximate the sensor. Temperature and humidity may also be measured with a hotplate sensor, which may or may not comprise a part of a system including the sensor. For instance, temperature may be directly measured from the resistance of a heater of a hotplate sensor. Humidity may be determined by measuring the thermal conductivity of air proximate the hotplate using the hotplate. In some embodiments, pressure may be derived from density detected by a resonant sensor or by measuring the deflection of a membrane over a sealed cavity. In some embodiments, a concentration of the one or more gases (other than the at least one analyte of interest) proximate the sensor may be determined with another sensor proximate the sensor.

In some embodiments, a sensor output may be calibrated according to Equation (1) below:

$$C = \left(S(T, P, H, C \,\&\, t) * \left(\frac{R_{comp}}{R_g} - 1\right)\right), \quad (1)$$

wherein C is the concentration of an analyte of interest in a gas sample, S(T, P, H, C & t) is a calibration factor for sensitivity of the gas sensor to the analyte of interest as a function of temperature, pressure, humidity, concentration of one or more gases (other than the analyte of interest) proximate the sensor, and time (T, P, H, & t, respectively), $R_{comp}$ is a compensated response (e.g., a compensated output resistance) of the sensor (i.e., an output of the sensor compensated for temperature, pressure, humidity, and concentration of the one or more gases based on respective compensation factors), and $R_g$ is the output resistance of the gas sensor responsive to exposure to a gas including the analyte of interest (i.e., the current sensor output).

FIG. 1 is a simplified flow diagram of a method 100 of measuring at least one property of an analyte of interest with a system comprising a sensor (e.g., a gas sensor), in accordance with embodiments of the disclosure. The method 100 includes act 102, including characterizing (e.g., in a factory) a sample set of sensors. Characterizing a sample set of sensors includes determining the sensitivity of one or more sensors of the sample set of sensors to one or more conditions proximate the one or more sensors, such as one or more of humidity, temperature, pressure over time, and concentration of one or more gases (other than the at least one analyte of interest); determining the sensitivity of the one or more sensors to one or more analytes of interest over time; and determining a correlation between the sensitivity of one or more sensors to at least one analyte of interest and the sensitivity of the one or more sensors to the one or more of temperature, pressure, humidity (e.g., absolute humidity, relatively humidity), and concentration of gases proximate the sensor over time; act 103 includes determining environmental compensation factors and calibration (e.g., gas calibrations) factors for a particular sensor (which may be different than the one or more sensors characterized in act 102) at the time of manufacture; act 104 including collecting raw data from the sensor, including the response (e.g., output) of the sensor over time, as well as humidity (e.g., absolute humidity), temperature, pressure, and concentration of one or more gases (H, T, P, and C) data proximate the sensor; act 106 including compensating the raw data from the sensor (e.g., the response of the sensor) for the effects of humidity (e.g., relative humidity), temperature, pressure, and concentration of one or more gases proximate the sensor using current compensation factors to determine a compensated sensor response; act 108 including determining a concentration of the at least one analyte of interest based on the compensated sensor response and current calibration factors; act 110 including, if the determined concentration of the at least one analyte of interest exceeds a predetermined value (threshold), outputting at least one property of the sample (e.g., the gas sample) proximate the sensor; and if the concentration of the at least one analyte of interest is below the predetermined value (i.e., no analyte gas detected), saving the raw sensor data below the predetermined value to a historical data file in the memory of the sensor; and act 112 including reviewing the saved historical data in the memory when the one or more analytes of interest are not present (the data of the historical data file) to determine the accuracy of the compensation factors and determine the current sensitivity of the sensor to one or more of humidity, temperature, pressure, and concentration of the one or more gases proximate the sensor; determining whether the current compensation factors are adequate and adjusting the compensation factors (FIG. 3B); adjusting the stored calibration factors for each analyte of interest based on the current sensitivity of the sensor to the one or more of humidity (e.g., absolute humidity, relative humidity), temperature, pressure, and the concentration of the one or more gases and the predetermined relationship between the sensitivity of the sensor to the one or more of humidity (e.g., absolute humidity, relative humidity), temperature, pressure, and the concentration of the one or more gases proximate the sensor and the sensitivity of the sensor to each respective analyte of interest.

Act 102 includes characterizing one or more sensors of a set of sensors to characterize properties of the one or more sensors based on exposure of the one or more sensors to various conditions (e.g., analyte of interest, sensor drift, aging, chemical history (e.g., exposure to various volatile organic compounds (VOCs)) and poisoning). Characterizing the one or more sensors includes determining the sensitivity of the one or more sensors to one or more conditions proximate the one or more sensors, such as one or more of temperature, pressure, humidity, or concentration of one or more gases (e.g., $CO_2$, CO, one or more VOCs) over time; determining the sensitivity of the one or more sensors to one or more analytes of interest over time; and determining a correlation between the sensitivity of the one or more sensors (e.g., one or more gas sensors) to at least one analyte (e.g., gas) of interest and the sensitivity of the one or more sensors to one or more conditions over the same time period. Characterizing the one or more sensors over the time period may include determining the sensitivity of the one or more sensors to one or more of temperature, pressure, humidity, the one or more gases, the at least one analyte of interest, and the correlation between the sensitivity of the sensor to the at least one analyte of interest and the sensitivity of the sensor to the one or more of humidity, temperature, pressure, and the one or more gases as the sensor ages during use and operation. In some embodiments, act 102 may further include determining initial compensation factors and calibration factors of the sensor based on the determined sensitivities. The initial compensation factors may be set such that a compensated output of the sensor remains substantially constant (e.g., within a predetermined range of values, exhibiting a percent change less than a predetermined amount, as described with reference to FIG. 5) responsive to exposure to a same sample (e.g., gas, such as a reference gas, a calibration gas, etc.), but at one or more of a different temperature, a different pressure, or a different absolute humidity. As will be described herein, the one or more sensors may include, for example, a gas sensor comprising a metal oxide semiconductor (MOS) sensor, a microhotplate sensor, a resonant sensor (e.g., a microcantilever sensor), an electrochemical sensor, a polymer sensor, an optical sensor, another sensor, or combinations thereof. The initial calibration factors may be based on the sensitivity of the one or more sensors to at least one analyte of interest. The sensor may include one or more of the sensors described in U.S. Patent Application 2018/0052124, the entire disclosure of which is hereby incorporated herein by this reference.

Figure 4A:
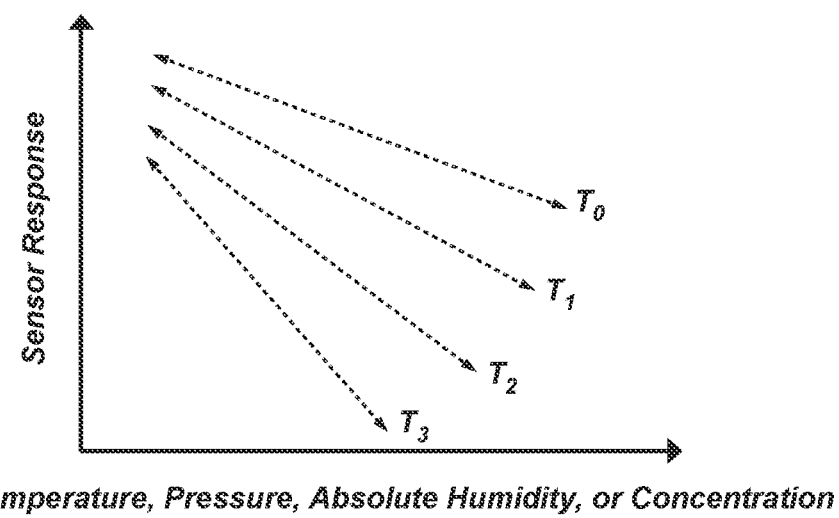
FIG. 4A is a graphical representation of a correlation between a sensitivity of a gas sensor to temperature, pressure, humidity, or concentration of one or more gases as a function of time ($T_0$, $T_1$, $T_2$, and $T_3$), in accordance with embodiments of the disclosure.
Figure 4B:
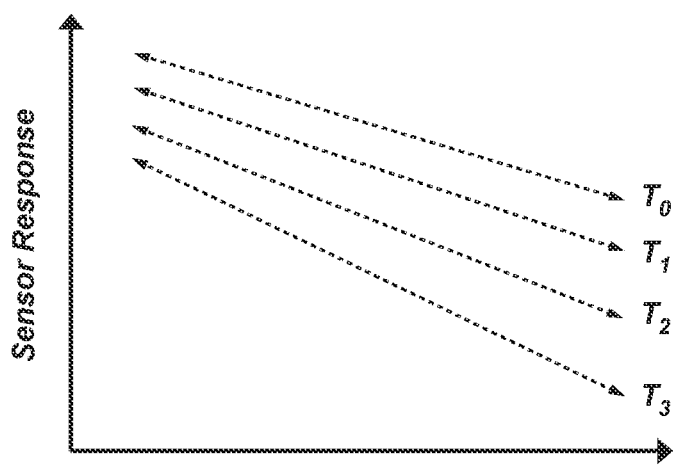
FIG. 4B is a graphical representation of the sensitivity of a gas sensor to an analyte gas of interest as a function of time ($T_0$, $T_1$, $T_2$, and $T_3$), in accordance with embodiments of the disclosure.

The correlation (e.g., relationship) between the sensitivity of the sensor to temperature, pressure, humidity (e.g., water), and the one or more gases (other than the at least one analyte of interest) and the sensitivity of the sensor to the at least one analyte of interest may be determined in a laboratory (e.g., at a factory). The correlation may be determined for each analyte of interest. In other words, different analytes may exhibit a different relationship between the sensitivity of the sensor to temperature, pressure, humidity, or the one or more gases over time (FIG. 4A) and the sensitivity of the sensor to the particular analyte of interest over time (FIG. 4B). In some embodiments, the correlation is determined for each sensor and each sensor may exhibit a unique correlation. In other embodiments, the correlation is determined with one or more representative sensors having, for example, the same composition (e.g., metal oxide coating materials, catalyst materials, or other coating materials) and make up (e.g., thermal mass) as other sensors in a fabricated batch of sensors. In some embodiments, sensors comprising different compositions (e.g., different metal oxide coating materials) may exhibit a different correlation. Act 102 may be performed once for a particular sensor type prior to production manufacture. In other embodiments, since it may be desirable to collect the characterization data over a long period of time, the one or more sensors may be configured to be updated and incorporate new characterization data through, for example, a communications port 718 (FIG. 7), which may facilitate downloading of the characterization data and characterization of the sensor when the one or more sensors are in use. In some embodiments, act 102 may facilitate production of a gas sensor without calibration for the at least one analyte of interest. In other words, and as will be described herein, the relationship between the sensitivity of the sensor to the at least one analyte of interest and the sensitivity of the sensor to one or more of humidity, temperature, pressure, and one or more gases, may be used to calibrate the sensor based on the relationship and the initial sensitivity of the sensor to the one or more of humidity, temperature, pressure, and the one or more gases (as opposed to exposure of the sensor to known concentrations of the at least one analyte of interest for calibration). For example, if the relationship between the sensitivity of the sensor to humidity and the sensitivity of the sensor to at least one analyte (e.g., gas) of interest is established, the humidity response of a sensor (e.g., the sensitivity of the sensor to humidity) may be used to establish the initial calibration factor for the at least one analyte (e.g., gas) of interest without the need to expose the sensor to the particular analyte of interest.

In some embodiments, determining the sensitivity of the one or more sensors to one or more of humidity, temperature, pressure, and the concentration of one or more gases proximate the sensor includes measuring a response of the one or more sensors while varying the one or more of the humidity, temperature, pressure, and concentration of the one or more gases proximate the sensor when the one or more sensors are exposed to a baseline sample (e.g., not including the at least one analyte of interest) at various times. For example, with reference to FIG. 4A, the sensitivity of the one or more sensors to the one or more of humidity, temperature, pressure, and concentration of one or more gases may be determined at times $T_0$, $T_1$, $T_2$, and $T_3$ (which may correspond to various stages of aging of the one or more sensors). The sensitivity of the one or more sensors to the one or more of humidity, temperature, pressure, and concentration of one or more gases at each time $T_0$, $T_1$, $T_2$, and $T_3$ may be represented as a slope of a curve (e.g., line) of the sensor response versus the respective one of the humidity, temperature, pressure, or gas concentration; or as an equation that is a function of the one or more of humidity, temperature, pressure, and gas concentration.

In other embodiments, the relationship between the temperature, pressure, humidity, or concentration of one or more gases and the output of the sensor (the sensitivity of the sensor to temperature, pressure, humidity, or the concentration of the one or more gases, respectively) may be represented as a non-linear equation. For example, in some embodiments, the relationship is represented as a non-linear equation wherein the extent of the sensor response decreases with increasing humidity, temperature, pressure, or concentration of the one or more gases. In other words, with increasing humidity, temperature, pressure, and concentration of the one or more gases, the rate of increase in the magnitude of the sensor response may decrease. In some such embodiments, the sensor may comprise a MOS sensor. In some embodiments, the sensitivity of the sensor to humidity, temperature, and pressure, may be expressed as an equation, such as for example, $S=1/X+A$, wherein S is the sensitivity, X is the humidity, temperature, pressure, or concentration of the one or more gases, and A is number, inclusive of zero, and may be positive or negative.

Figure 3A:
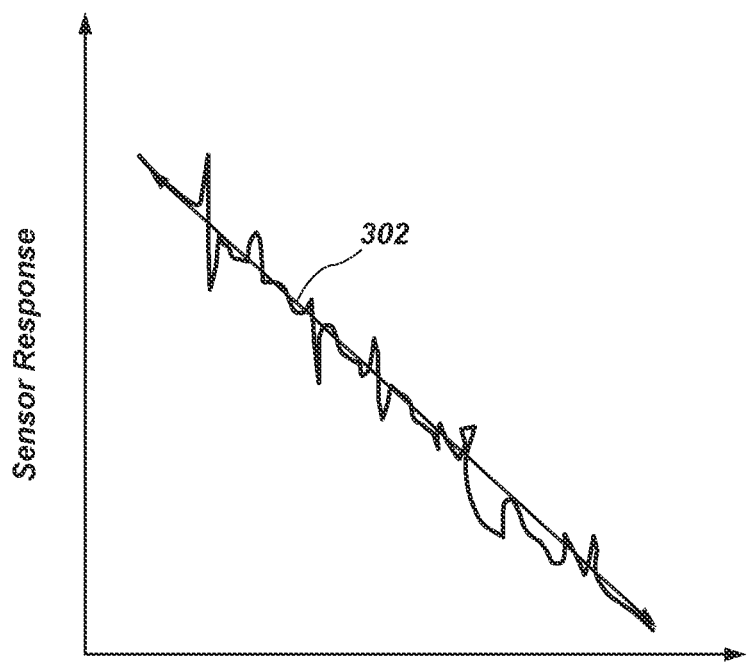
FIG. 3A, FIG. 3B and FIG. 3C are graphical representations of a sensitivity of a gas sensor to temperature, pressure, humidity, or a concentration of one or more gases proximate the gas sensor, in accordance with embodiments of the disclosure.

In some embodiments, the sensitivity of the one or more sensors to one or more conditions proximate the sensor (e.g., one or more of humidity, temperature, pressure, and the concentration of the one or more gases proximate the sensor) may be determined by maintaining a negligible or constant concentration of the analyte of interest (e.g., less than about 1 ppm, about 0 ppm, etc.) proximate the one or more sensors and measuring an output (e.g., the resistance, such as the change in resistance relative to the baseline resistance ($\Delta R$), a change in conductance ($\Delta G$), the change in resonant frequency, the change in voltage, the change in current, etc.) of the one or more sensors responsive to changes in the one or more of humidity, temperature, pressure, and concentration of the one or more gases proximate the one or more sensors. FIG. 3A is a graphical representation illustrating the sensitivity of a sensor to temperature, pressure, humidity, or concentration of one or more gases proximate the sensor in an ambient atmosphere (e.g., outside the presence of an analyte of interest), which may be simulated in a laboratory to establish parameters used for calibration. An output of the sensor (e.g., a resistance of the gas sensor, a change in resonant frequency of the gas sensor, a change in voltage of the gas sensor, a change in current of the gas sensor, a change in conductance of the gas sensor) may be measured, such as with electrodes of the sensor. The output of the sensor (such as, for example, a log of the resistance of the sensor) may be plotted against the temperature, pressure, humidity, or concentration of the one or more gases proximate the sensor. A relationship between the temperature, pressure, humidity, or concentration of gases and the output of the sensor may be determined and is represented as a line having a slope, an x-intersect, and a y-intersect, as indicated by arrow 302, wherein the sensitivity of the sensor to the temperature, pressure, humidity (e.g., water), or concentration of gases is represented as the slope of the line illustrated. With continued reference to FIG. 3A, (derived from field data) the response of the sensor may exhibit background noise, which may be caused by a presence of gases proximate the sensor while the temperature, pressure, humidity varies, or concentration of gases. Such background noise may be removed by averaging or low pass filtering the response of the sensor. Outlier points or noise caused by interfering gases shown on FIG. 3A may be removed to increase the accuracy of the response of the sensor to only the temperature, pressure, humidity, or concentration of gases.

Figure 3B:
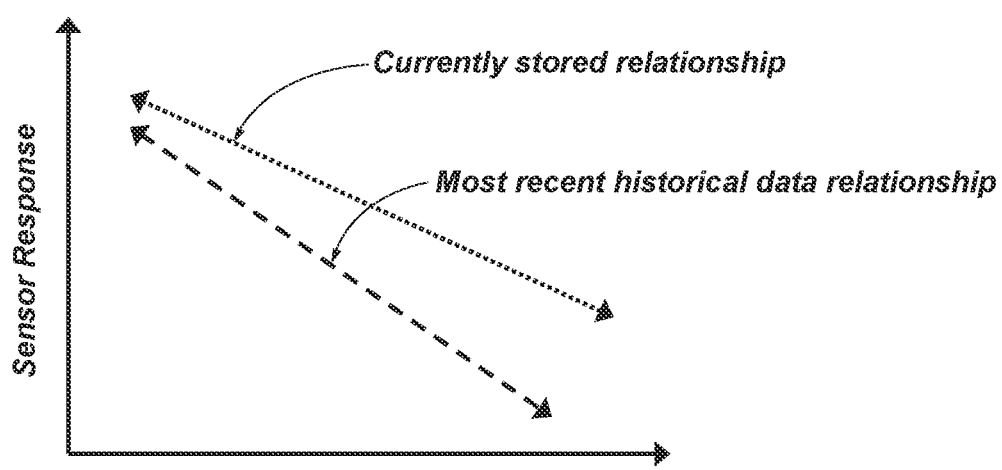
Figure 3C:
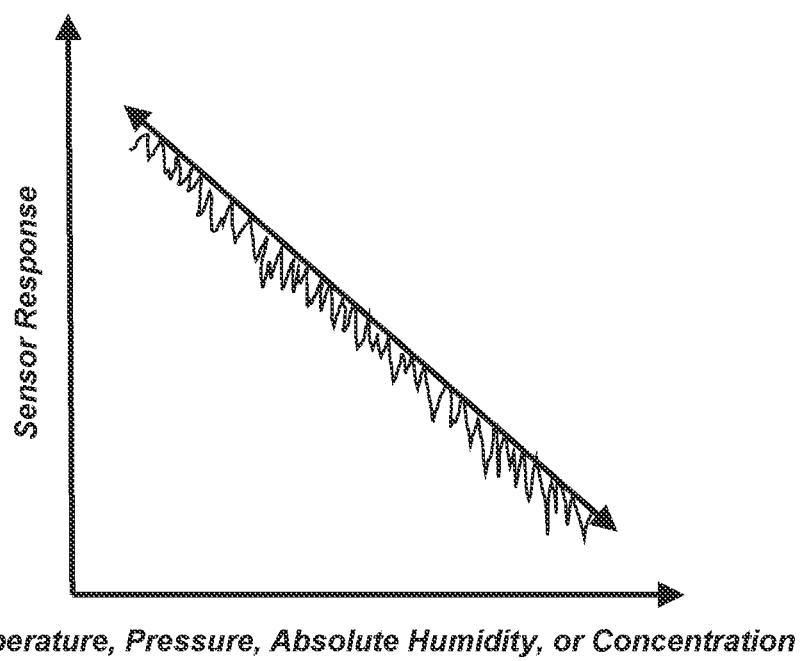

In some embodiments, determining the sensitivity of the sensor to one or more conditions proximate the sensor (e.g., the one or more of temperature, pressure, humidity (water concentration), and/or concentration of one or more gases) may include signal processing or conditioning as is known in the art, such as low-pass filtering or averaging the output of the sensor to remove short-term variations of the output of the sensor. For example, referring to FIG. 3A, short-term sensor variations as a result of sensor noise or response to other gases in the ambient environment are illustrated superimposed on the line 302. Such short-term variations may be due to the presence of interfering analytes present during measurements. Averaging or low-pass filtering may remove or reduce the impact of the short-term variations and may increase the signal-to-noise ratio of the sensor. A regression analysis, for example, may be used to determine the underlying relationship between the one or more of humidity, temperature, pressure, or concentration of one or more gases proximate the sensor and sensor output. In some embodiments, the sensitivity to the one or more of humidity, temperature, pressure, or concentration of one or more gases proximate the sensor is determined when the one or more analytes of interest are not present and there is a change in environmental conditions. In other embodiments, data obtained with the sensor is not exposed to the analyte of interest and data obtained when the sensor is exposed to the analyte of interest may be used together to determine the sensitivity of the sensor to humidity, temperature, pressure, or concentration of one or more gases proximate the sensor. Noise in the sensor response may be caused by the presence of trace amounts of gases (such as volatile organic compounds) to which the sensor responds as shown in FIG. 3C. In this example, a more accurate slope of the response may be obtained by averaging the minimum responses of the sensor as shown in FIG. 3C.

In some embodiments, the log of the temperature, pressure, concentration of water (humidity), or concentration of one or more gases proximate the sensor may exhibit a linear relationship with a log of a resistance measured by the sensor. However, the disclosure is not so limited and the sensitivity of the sensor to temperature, pressure, humidity, or concentration of one or more gases proximate the sensor may be other than linear.

In some embodiments, determining the sensitivity of the one or more sensors to the at least one analyte of interest includes measuring a response of the one or more sensors while varying the concentration of the at least one analyte of interest proximate the one or more sensors. For example, with reference to FIG. 4B, the sensitivity of the one or more sensors to the at least one analyte of interest may be determined at $T_0$, $T_1$, $T_2$, and $T_3$ (e.g., corresponding to the same times $T_0$, $T_1$, $T_2$, and $T_3$ described above with reference to FIG. 4A). The sensitivity of the one or more sensors to the at least one analyte of interest at each time $T_0$, $T_1$, $T_2$, and $T_3$ may be represented as a slope of a curve (e.g., line) or as an equation that is a function of the concentration of the at least one analyte of interest.

Accordingly, in some embodiments, the sensitivity of the sensor to exposure to the analyte of interest may correspond to the slope (or an absolute value of the slope) of a line showing the relationship between the concentration of the analyte of interest and the output (e.g., the resistance) of the sensor, similar to FIG. 4B, wherein the x-axis is the log of the concentration of the analyte of interest and the y-axis is the log of the output of the sensor.

Figure 2A:
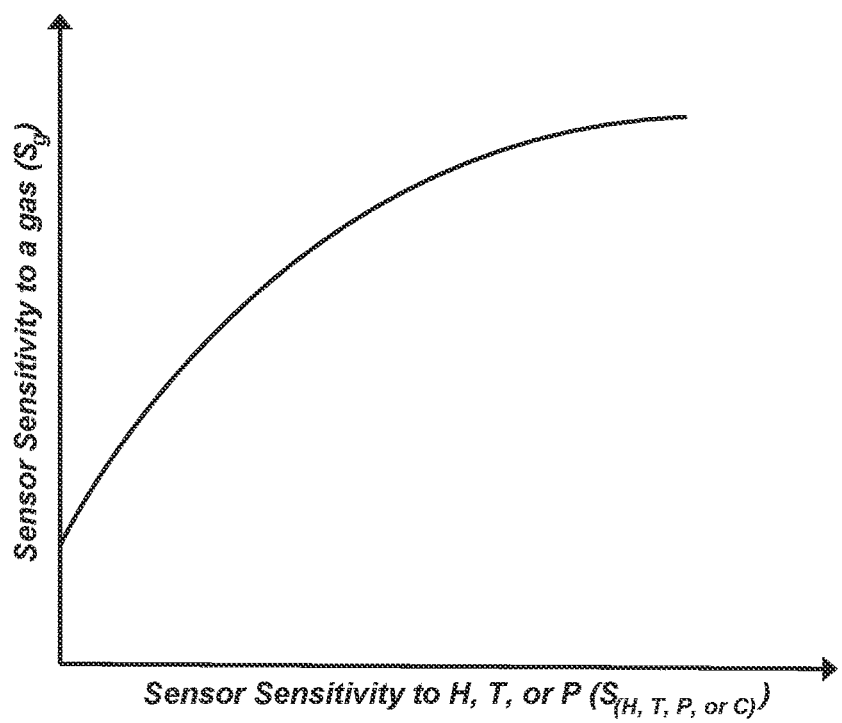
FIG. 2A is a graphical representation illustrating a relationship between a sensitivity of a sensor to one of humidity, temperature, pressure, or a concentration of one or more gases (other than an analyte of interest) proximate the sensor to the sensitivity of the sensor to an analyte of interest ($S_g$), in accordance with embodiments of the disclosure.

With continued reference to FIG. 1, determining the relationship between the sensitivity of the one or more sensors to the one or more of humidity, temperature, pressure, and concentration of one or more gases proximate the sensor to the sensitivity of the one or more sensors to the at least one analyte of interest includes, for example, determining the sensitivity of the one or more sensors to the at least one analyte of interest as a function of one or more of the sensitivity of the sensor to the one or more of humidity, temperature, pressure, and the concentration of the one or more gases proximate the sensor. For example, FIG. 2A is a graphical representation of the relationship between the sensitivity of the sensor to the one or more of humidity, temperature, pressure, and concentration of one or more gases ($S_H$, $S_T$, $S_P$, $S_C$, respectively), to the sensitivity of the sensor to the at least one analyte (e.g., gas) of interest ($S_g$). The ratio corresponds to the slope of the curve at any particular point. In other words, for a given sensitivity of the sensor to one or more of humidity, temperature, pressure, and concentration of one or more gases, the ratio may correspond to the corresponding sensitivity of the sensor to the at least one analyte (e.g., gas) of interest divided by the sensitivity of the sensor to the one or more of humidity, temperature, and pressure, and concentration. In FIG. 2A, the sensitivity of the sensor to the one or more of humidity, temperature, and pressure may be graphed against the sensitivity of the sensor to the at least one analyte of interest. The sensitivity of the sensor to the one or more of humidity, temperature, pressure, and concentration may be determined as described above (e.g., with respect to FIG. 3A through FIG. 3C, and FIG. 4A). For each value of the sensitivity of the senor to the one or more of humidity, temperature, pressure, and concentration, the sensitivity of the sensor to the at least one analyte of interest may be determined, as described above (e.g., with respect to FIG. 4B, for example).

Figure 2B:
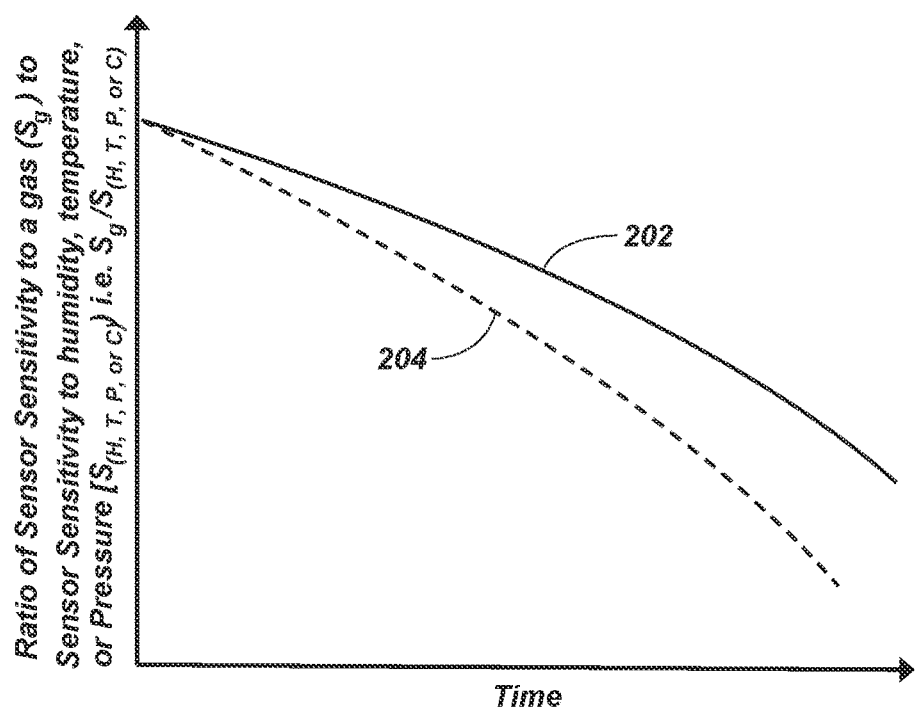
FIG. 2B is a graphical representation illustrating changes in a ratio of a sensitivity of a sensor to a gas ($S_g$) to the sensitivity of the sensor to temperature, pressure, humidity, or concentration of one or more gases ($S_{(T, P, H, or C)}$) over time, in accordance with embodiments of the disclosure.

FIG. 2B is a graphical representation of how the ratio of the sensor sensitivity to at least one analyte (e.g., gas) and the sensor sensitivity to temperature, pressure, humidity, or concentration (other than of the at least one analyte of interest) may vary over time. Curve 202 may be derived by measuring (e.g., monitoring) the response of the sensor to temperature, pressure, humidity, or concentration over time ($T_0$, $T_1$, $T_2$, $T_3$) when there is no analyte present in the gas proximate the sensor (as shown and described with reference to FIG. 4A) and measuring the response of the sensor to an analyte gas of interest over the same period of time ($T_0$, $T_1$, $T_2$, $T_3$) (as shown and described with reference FIG. 4B). The points of curve 202 represent the ratio of the response of the sensor to exposure to the analyte of interest to the response of the sensor to changes in the one or more of temperature, pressure, humidity, and concentration over the same duration at a given time. For example, each point on curve 202 represents the relationship illustrated in FIG. 2A and the curve 202 represents the relationship over several periods of time. In some embodiments, an equivalent signal having no analyte (e.g., gas) in the response can be obtained by subtracting the portion of the signal due to the presence of the analyte (e.g., gas).

Figure 7:
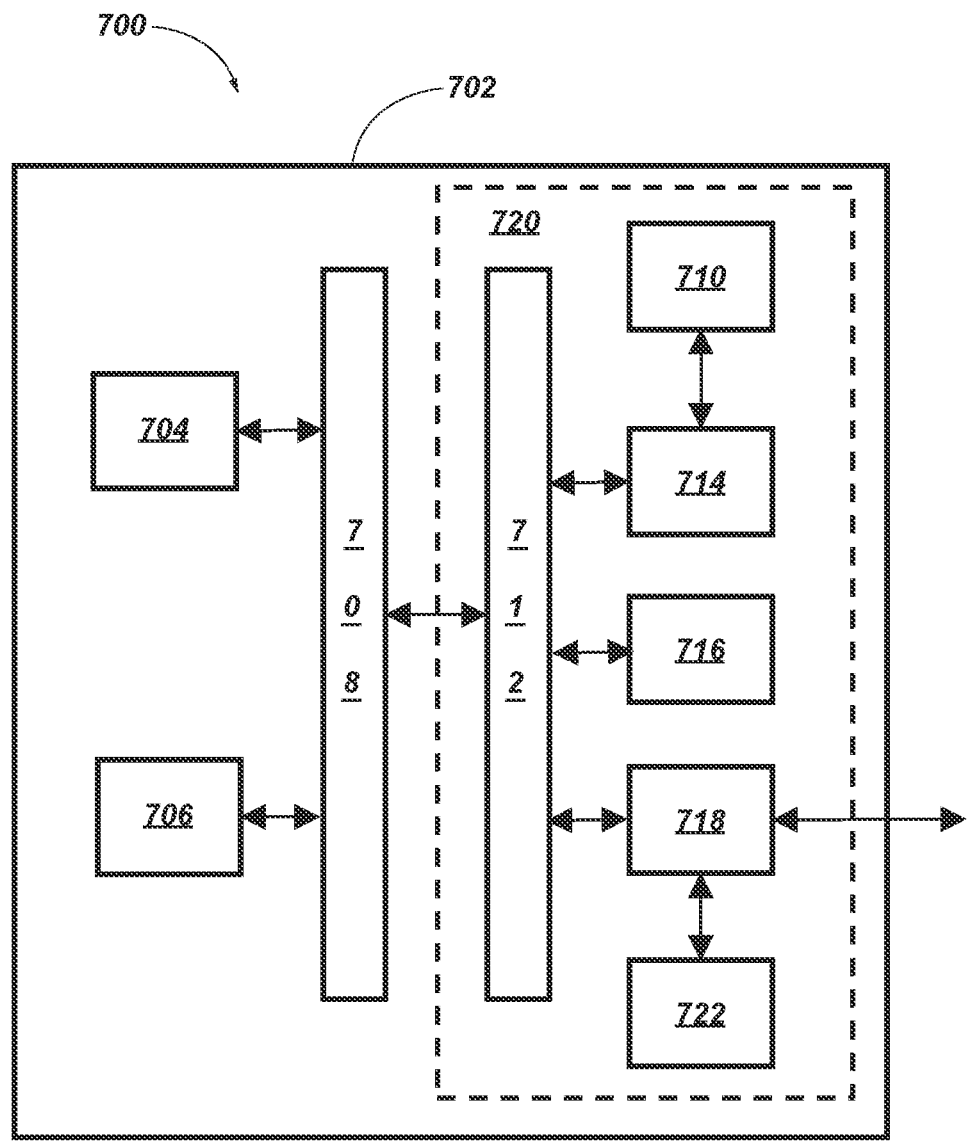
FIG. 7 is an overall block diagram of a detector including one or more gas sensors, in accordance with embodiments of the disclosure.

With continued reference to FIG. 2B, curve 204 may be derived as a function of the aging of the sensor, such as a function of the exposure history of the sensor to a variety of gases such as volatile organic compounds (VOCs) (e.g., VOCs ppm-hours), known poisoning gases, and various environmental conditions (e.g., ° K-hours, kilo-pascal-hours). The exposure history of the sensor can include peak exposure concentration, average exposure concentrations, and total dosage exposure (e.g., ppm-hours) to various gases. In some embodiments, the ratio $S_g/S_{(T, P, H, or c)}$ may be adjusted based on the total dosage or exposure experienced by the sensor. The response of the sensor to the total dosage of gases and environmental conditions to which the sensor is exposed may be predetermined or characterized at the factory, as indicated at act 102. These responses may also be periodically updated to units in the field via a communications port 718 (FIG. 7). In some embodiments, curve 204 may be derived by characterizing the relationship between the sensitivity of the sensor to the at least one analyte of interest to the sensitivity of the sensor to the one or more of humidity, temperature, pressure, and concentration of one or more gases (other than the at least one analyte of interest) with several sensors, each sensor exposed to varying levels of aging (e.g., various levels of poison gases). Each sensor exposed to a particular amount of aging may correspond to a particular curve 204. In some embodiments, a processing subsystem of the sensor is configured to use an appropriate relationship between the sensitivity of the sensor to the at least one analyte of interest to the sensitivity of the sensor to the one or more of humidity, temperature, pressure, and concentration based on the aging of the sensor.

Although FIG. 2A illustrates relationship between the sensitivity of the sensor to temperature, pressure, humidity, or concentration and the sensitivity of the sensor to the analyte of interest and FIG. 2B illustrates the relationship between the sensitivity of the sensor to temperature, pressure, humidity, or concentration and the sensitivity of the sensor to the analyte of interest over time graphically, in other embodiments, the relationships may be in the form of a look-up table. In some such embodiments, for a given sensitivity of the sensor to temperature, pressure, humidity, or concentration over time; the look-up table may include a corresponding value (e.g., a factor) of the sensitivity of the sensor to the analyte of interest over time.

In some embodiments, the relationship between the sensitivity of the sensor to humidity, temperature, pressure, or the concentration of the one or more gases (other than the at least one analyte of interest) proximate the sensor and the sensitivity of the sensor to the at least one analyte of interest may be in the form of a mathematical equation. By way of nonlimiting example, in some such embodiments, the relationship between the sensitivity of the sensor humidity, temperature, pressure, and concentration of one or more gases proximate the sensor and the sensitivity of the sensor to the at least one analyte of interest (illustrated as a curve in FIG. 2A and illustrated by the y-axis in FIG. 2B) may be represented as a mathematic formula. The relationship may be determined based on one or both of the time the sensor has been exposed to various samples and the current sensitivity of the sensor to the one or more of temperature, pressure, humidity, and concentration of the one or more gases proximate the sensor. As only one nonlimiting example, the relationship may be represented as $S_g=B*S_X$, wherein $S_g$ is the same as described above, $S_X$ is the sensitivity of the sensor to one of humidity, temperature, pressure, and concentration of the one more gases proximate the sensor and B is a factor (e.g., a multiplication factor, such as a number), indicating that the sensitivity of the sensor to the at least one analyte of interest increases with an increase in the sensitivity of the sensor to the one or more of humidity, temperature, pressure, and concentration of the one or more gases. As another nonlimiting example, in some embodiments, the relationship may be represented as $S_g=S_X^{(1-C)}$, wherein $S_g$ and $S_X$ are the same as before, and C is a factor.

With reference to FIG. 2B, the relationship between the sensitivity of the sensor to temperature, pressure, humidity, and concentration of one or more gases (other than the at least one analyte of interest) and the sensitivity of the sensor to the analyte of interest may be determined by determining the sensitivity of the sensor to temperature, pressure, humidity, and concentration and determining the sensitivity of the sensor to the analyte of interest and plotting the ratio of these sensitivities as a function of time. For example, with reference to FIG. 4A, the sensitivity of the sensor to temperature, pressure, humidity, or concentration of the one or more gases may be determined at multiple times (e.g., time $T_0$, time $T_1$, time $T_2$, time $T_3$, etc.) by measuring the response of the sensor to exposure to different environmental conditions at such times, as described above. Each time (e.g., time $T_0$, time $T_1$, time $T_2$, time $T_3$, etc.) may represent a duration over which multiple measurements are made by the sensor. Similarly, and with reference to FIG. 4B, the sensitivity of the sensor to the at least one analyte of interest may be determined at multiple times (e.g., time $T_0$, time $T_1$, time $T_2$, time $T_3$, etc.), which may be the same times (e.g., durations) as described with reference to determining the sensitivity of the sensor to temperature, pressure, humidity, or concentration, by measuring the response of the sensor to exposure to different concentrations of the at least one analyte of interest. In other words, FIG. 4A graphs the sensor response on the y-axis versus the temperature, pressure, humidity, or concentration of one or more gases (other than the analyte of interest) on the x-axis, and FIG. 4B graphs the sensor response on the y-axis (i.e., the same sensor response of FIG. 4A) and the concentration of the analyte of interest on the x-axis. The ratio of the sensitivity of the sensor to the analyte of interest to the sensitivity of the sensor to the one or more of humidity, temperature, pressure, and concentration at a given time is represented as a curve in FIG. 2A and as a point in FIG. 2B. For example, at time $T_0$, the slope of the line labeled $T_0$ in FIG. 4A is the x-value of a point of the correlation illustrated in FIG. 2B at a time corresponding to $T_0$, wherein the corresponding y-value is the slope of the line labeled $T_0$ (or at a time immediately after time $T_0$) in FIG. 4B. In other words, at time $T_0$, the y-value of a point on one of the curves 202, 204 of FIG. 2B corresponding to time $T_0$ is the slope of the line labeled $T_0$ in FIG. 4B divided by the slope of the line labeled $T_0$ in FIG. 4A. The process of measuring both of the sensitivity of the sensor to temperature, pressure, humidity, or concentration and the sensitivity of the sensor to the analyte of interest to generate another point in FIG. 2B may be repeated a sufficient number of times to generate a relationship (correlation) between the sensitivity of the sensor to temperature, pressure, humidity, and concentration and the sensitivity of the sensor to the analyte of interest as a function of time. The difference in time between each $T_0$, $T_1$, $T_2$, and $T_3$ may be days, weeks, months, or years and may represent different levels of aging of the sensor.

In some embodiments, the relationship between the sensitivity of the sensor to the one or more of humidity, temperature, pressure, and concentration of one or more gases (other than the at least one analyte of interest) proximate the sensor to the sensitivity of the sensor to the at least one analyte of interest are not linear over a range of the one or more of the humidity, temperature, pressure, concentration of the one or more gases, and the concentration of the at least one analyte of interest, the relationship may be represented as an equation. For example, the sensitivity of the sensor to the at least one analyte of interest may be represented as a first equation. Similarly, the sensitivity of the sensor to the one or more of humidity, temperature, pressure, and the concentration of the one or more gases proximate the sensor may be represented as a second equation. The relationship between the sensitivities may be represented as a derivative of the first equation to the derivative of the second equation. In other words, the local sensitivity (or slope) of the sensor at each point in the curves of FIG. 4B and FIG. 4A may be represented as the respective derivative of the first equation and the derivative of the second equation. In yet other embodiments, the average sensitivity of the sensor to each of the at least one analyte of interest and the one or more of humidity, temperature, pressure, and concentration of the one or more gases may be averaged, such as by boxcar averaging the sensitivity curves. In further embodiments, a non-linear sensitivities may be approximated with a linear relationship (e.g., as illustrated in FIG. 4A and FIG. 4B).

In some embodiments, the process can be repeated daily, monthly or over a number of years to generate sufficient data to determine the relationship illustrated in FIG. 2B. Hence, a relationship between the sensitivity of the sensor to temperature, pressure, humidity, or concentration of one or more gases proximate the sensor versus the sensitivity of the sensor to the analyte is established and can subsequently be used to calibrate the sensor response to the analyte based on the sensitivity of the sensor to temperature, pressure, humidity, or concentration of gases, as will be described herein. A most recent sensitivity of the sensor to the analyte of interest may be determined at the factory to calibrate the sensor and may correspond to the initial calibration factor.

In some embodiments, the sensitivity of the sensor to exposure to the at least one analyte of interest may be determined as a function of humidity by maintaining a predetermined concentration of humidity (about 0 ppm, less than about 10 ppm water, less than about 100 ppm, less than about 500 ppm, less than about 1,000 ppm, etc.) proximate the sensor and measuring an output (e.g., the resistance, such as the change in resistance relative to the baseline resistance ($\Delta R$), a change in conductance ($\Delta G$), the change in resonant frequency ($\Delta F$), the change in voltage ($\Delta V$), the change in current ($\Delta I$)) of the sensor responsive to changes in the concentration of the analyte of interest to determine the sensitivity of the sensor to the analyte of interest at the predetermined concentration of humidity. In some embodiments, the concentration of humidity may be negligible, such as less than about 10 ppm or about 0 ppm. In other embodiments, the concentration of humidity may be greater than about 1,000 ppm, greater than about 2,000 ppm, greater than about 5,000 ppm, or even greater than about 10,000 ppm. Determining the sensitivity of the sensor to the at least one analyte of interest at several humidity levels may facilitate calibrating the sensor response for the humidity proximate the sensor. Stated another way, the response of the sensor to exposure to at least one analyte of interest may be dependent on the humidity level proximate the sensor when the sensor is exposed to the at least one analyte of interest. In other words, in some embodiments, the sensitivity of the sensor to the at least one analyte of interest may be dependent not only on the sensitivity of the sensor to the one or more of humidity, temperature, pressure, and concentration of one or more gases proximate the sensor; but also on the background humidity at which the sensor response is measured. Determining the sensitivity of the sensor to the at least one analyte of interest at varying humidity levels may facilitate improved calibration of the response of the sensor. For example, in some embodiments, the response of the sensor may be calibrated differently (e.g., with a different mathematical formula, with a different calibration factor, with a different offset) based on the humidity level measured when the sensor is exposed to the at least one analyte of interest. Normal day-to-day variations in humidity provide varied sensor responses that may be used to adjust the sensitivity of the sensor to the analyte of interest (calibration factor), as will be described herein. In some embodiments, such as part of a factory calibration, humidity may be applied intentionally as a calibration gas.

With reference back to FIG. 1, act 103 includes determining the initial environmental compensation factors and the calibration factors (e.g., gas calibration factors) for a particular (e.g., a new) sensor at the time of manufacture. As will be described herein, the initial environmental compensation factors and the initial calibration factors establish the starting point before the iterative updating processes of act 104 through act 112 for calibrating and compensating the sensor response during use and operation of the sensor. In some embodiments, act 103 is omitted if the sensor characterization data is sufficient to initialize the compensation and calibration factors. Stated another way, in some embodiments, act 102 may include determining the initial environmental compensation factors and calibration factors of the sensor (such that the initial environmental compensation factors and calibration factors are not determined for each particular sensor). For example, the initial sensitivity of the sensor to one or more of humidity, temperature, pressure, and concentration of the one or more gases (other than the at least one analyte of interest) and the known relationship between the sensitivity of the sensor to at least one analyte of interest and the sensitivity of the sensor to the one or more of humidity, temperature, pressure, and the concentration of the one or more gases may be used to determine the initial calibration factors. In other embodiments, water vapor may be used as a calibration gas to determine the initial calibration factors, based on the known relationship between the sensitivity of the sensor to the at least one analyte of interest and the sensitivity of the sensor to humidity.

In some embodiments, act 103 further includes determining initial environmental compensation factors for each of temperature, pressure, humidity, and concentration of one or more gases (other than the at least one analyte of interest) as well as gas calibration factors at the time the sensor is manufactured. Determining the compensation factor for each parameter may include maintaining a composition (e.g., an ambient gas substantially free of the analyte of interest) proximate the sensor and changing the particular parameter (e.g., one of the temperature, pressure, humidity, and gas concentration) proximate the sensor while measuring the output of the sensor. For example, to determine the compensation factor for temperature, the sensor may be exposed to a reference gas (e.g., an ambient gas) and the temperature proximate the sensor may be changed while the response of the sensor is measured. A temperature compensation factor may be derived such that a relationship between the temperature compensation factor and the response of the sensor yields a compensated response of the sensor, wherein the compensated response of the sensor is substantially constant (i.e., within a predetermined range, such as less than about plus or minus about 5%) when a temperature proximate the sensor changes (while other conditions, such as composition, pressure, and humidity, proximate the sensor remain substantially constant). Stated another way, the temperature compensation factor may be determined such that the response of the sensor may be compensated with the temperature compensation factor to yield a compensated response of the sensor, the compensated response of the sensor remaining substantially constant when the sensor is exposed to changing temperatures. In some embodiments, the compensation factors for humidity, temperature, and pressure are different than the sensitivity of the sensor to the respective one of the humidity, temperature, and pressure. In some embodiments, the sensitivity of the sensor to the one or more of humidity, temperature, and pressure may be used to compensate the sensor to the effects of humidity, temperature, and pressure, respectively, using, for example, algorithmic logic, equations, or other relationships.

To determine the compensation factor for pressure, the sensor may be exposed to a reference (e.g., an ambient gas) and the pressure may be changed while the response of the sensor is measured. A pressure compensation factor may be derived such that a relationship between the pressure compensation factor and the response of the sensor yields a compensated response of the sensor, wherein the compensated response of the sensor is substantially constant (i.e., within a predetermined range, such as less than about plus or minus about 5%) when a pressure proximate the sensor changes.

To determine the compensation factor for humidity, the sensor may be exposed to a reference gas (e.g., an ambient gas) and the humidity may be changed while the response of the sensor is measured. A humidity compensation factor may be derived such that a relationship between the humidity compensation factor and the response of the sensor yields a compensated output of the sensor, wherein the compensated response of the gas sensor is substantially constant (i.e., within a predetermined range, such as less than about plus or minus about 5%) when a humidity proximate the sensor changes.

To determine the compensation factor for concentration of a gas (other than the at least one analyte of interest), the sensor may be exposed to a reference gas (e.g., an ambient gas having a baseline humidity, temperature, and pressure) and the concentration of the gas may be changed while the response of the sensor is measured. A concentration compensation factor may be derived such that a relationship between the concentration compensation factor and the response of the sensor yields a compensated output of the sensor, wherein the compensated response of the gas sensor is substantially constant (i.e., within a predetermined range, such as less than about plus or minus about 5%) when a concentration of the gas proximate the sensor changes.

In some embodiments, the compensation factor for each of humidity, temperature, pressure, and gas concentration may be determined using linear regression, or another method of fitting the compensated response of the sensor to be within a predetermined range based on changes in the respective compensation factors.

Figure 5:
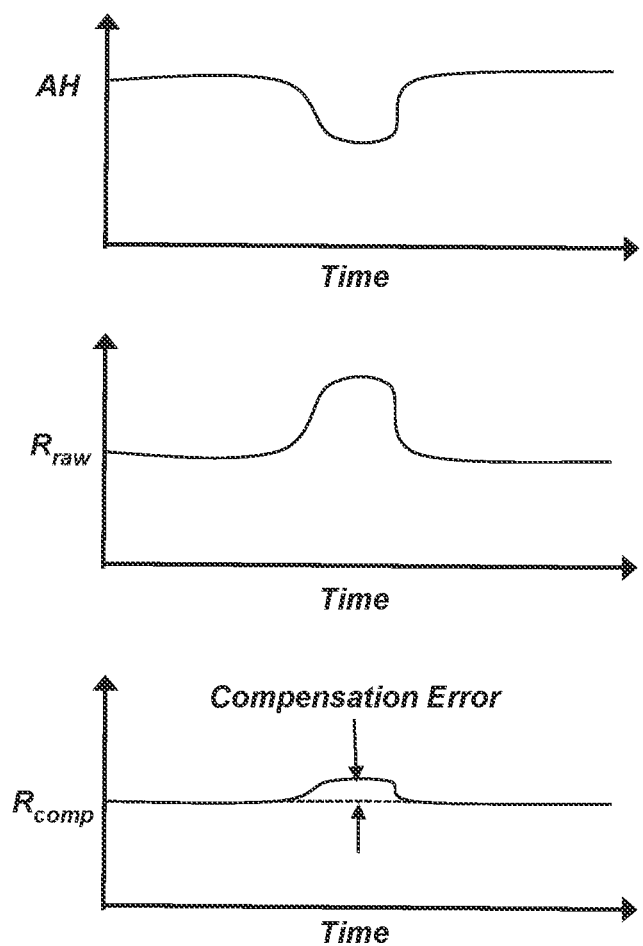
FIG. 5 illustrates changes in absolute humidity (AH) and the corresponding changes in the sensor resistance ($R_{raw}$) and the compensated sensor resistance ($R_{comp}$) of a sensor, in accordance with embodiments of the disclosure.

For example, FIG. 5 is a simplified illustration of the relationships between absolute humidity (AH), the raw sensor data ($R_{raw}$) (the uncompensated and uncalibrated response of the sensor), and the compensated sensor data ($R_{comp}$). The $R_{comp}$ plot in this illustration shows a compensation error in response to a humidity change when no other gases are present. An accuracy of the compensation factor for humidity may be determined using the relationships illustrated in FIG. 5. In other words, the value of the current compensation factor for humidity may be adjusted such that the compensated sensor data ($R_{comp}$) is relatively flat when the sensor is not exposed to any VOCs or analytes of interest (i.e., the analytes of interest are not present), even with changing humidity. Similarly, the current compensation factor for temperature, pressure, and gas concentration (for gases other than the at least one analyte of interest) may be adjusted in a similar manner. The presence of a compensation error such as shown in FIG. 5 can be used as a trigger to perform adjustment of the compensation factors as described with reference to act 112.

With continued reference to FIG. 1, act 104 includes collecting raw data from the sensor, including sensor responses, temperature, pressure, humidity (e.g., absolute humidity, relative humidity), and concentration of one or more gases (other than the at least one analyte) proximate the sensor data. Act 104 may include collecting raw data from the sensor (e.g., $R_{raw}$) and from one or more environmental sensors. The sensor and the environmental sensor may be exposed to a sample and the output signal of the sensor may be collected. The raw data may be an output signal (i.e., a response) of the sensor responsive to exposure to the sample. The sample may be a sample from the atmosphere proximate a location of the sensor. Act 104 may include collecting the raw data from a system including the sensor by measuring the response of the sensor and measuring a temperature, a pressure, and a relative humidity proximate the sensor. The temperature, pressure, and relative humidity may be measured with, for example, an environmental sensor proximate the sensor. Measuring the response of the sensor may include measuring a resistance change of the sensor. In other embodiments, measuring the response of the sensor may include measuring a resonant parameter (e.g., a resonant frequency) of the sensor.

The concentration of water vapor (e.g., the humidity) proximate the sensor at a given time may be determined with, for example, one or more environmental sensors located proximate the sensor. By way of nonlimiting example, the humidity (e.g., water concentration) proximate the sensor may be determined with a humidity sensor configured to measure an absolute humidity. In other embodiments, a temperature, a pressure, and a relative humidity proximate the sensor may be measured, such as with a temperature sensor, a pressure sensor, and a relative humidity sensor proximate the sensor. The concentration of water (humidity) proximate the sensor may be determined based on the current temperature, pressure, and relative humidity proximate the sensor using mathematical equations correlating the temperature, pressure, and relative humidity to the absolute humidity. In some embodiments, temperature and humidity may be measured with a hotplate sensor, which may or may not comprise a part of a system including the gas sensor. By way of nonlimiting example, temperature can be directly measured from the resistance of a heater of the hotplate sensor. Humidity may be measured by measuring the thermal conductivity of the ambient air with a hotplate. Pressure may be derived from the density or viscous damping detected by a resonant sensor or by measuring the deflection of a diaphragm over a sealed cavity. In some embodiments, the concentration of one or more gases proximate the sensor (other than the at least one analyte of interest) may be measured with one or more additional gas sensors proximate the sensor for measuring the concentration of the at least one analyte of interest. In some embodiments, in addition to the sensor, a single silicon die may include each of a hotplate sensor for determining the temperature and humidity and one of a resonant sensor and/or a diaphragm over a sealed cavity for determining the pressure.

In some embodiments, one or more of the temperature, the pressure, the concentration of humidity, and the concentration of one or more gases proximate the sensor may be measured at regular intervals, such as every about 1 hour, every about 30 minutes, every about 15 minutes, every about 5 minutes, every about 1 minute, every about 30 seconds, every about 5 seconds, every about 2 seconds, every about 1 second, or another interval. In some embodiments, the one or more of the temperature, the pressure, the concentration of humidity, and the concentration of the one or more gases is determined every about 2 seconds. However, the disclosure is not so limited and such properties may be determined at different intervals. In some embodiments, the one or more of the temperature, pressure, the concentration of humidity, and the concentration of the one or more gases is measured at random intervals that may not be evenly spaced. The resistance change of the sensor ($\Delta R$), a change in conductance ($\Delta G$), the change in resonant frequency ($\Delta F$) of the sensor, the change in voltage ($\Delta V$) of the sensor, or the change in current ($\Delta V$) of the sensor may computed each time the one or more of the temperature, the pressure, the concentration of humidity, and the concentration of the one or more gases is determined to determine the current sensitivity of the sensor to the respective one or more of the temperature, the pressure, the concentration of humidity, or the concentration of the one or more gases.

Act 106 includes compensating the raw data for effects of humidity (e.g., relative humidity), temperature, pressure, or the concentration of one or more gases proximate the sensor using current (e.g., the most recent) compensation factors for each of humidity, temperature, pressure, or concentration of the one or more gases to determine a compensated sensor response. Compensating the raw data may include adjusting the raw data such that the compensated sensor response remains substantially constant when exposed to the ambient gas proximate the sensor with respect to changes in temperature, pressure, humidity, and/or concentration of the one or more gases (other than the at least one analyte of interest) proximate the sensor. In some embodiments, the raw data may be compensated with the initial compensation factors (determined during act 102). In other embodiments, and as will be described herein, the raw data may be compensated with one or more adjusted compensation factors.

One embodiment of a generalized mathematical formula of the compensation of the sensor output for environmental effects (of humidity, temperature, pressure, and concentration of one or more gases (other than the at least one analyte of interest) proximate the sensor) is shown in Equation (2) below:

$$R_{comp} = R_{raw} * \left[ \left(\frac{AH_n}{AH_0}\right)^Q * \left(\frac{T_n}{T_0}\right)^W * \left(\frac{P_n}{P_0}\right)^Z * \left(\frac{C_n}{C_0}\right)^X \right], \quad (2)$$

wherein $R_{comp}$ is the compensated output of the sensor, $R_{raw}$ is the raw sensor output, $AH_n$ is the absolute humidity currently measured, $AH_0$ is a baseline or starting absolute humidity (the absolute humidity at which the sensor was baselined), Q is the humidity compensation factor, $T_n$ is the current temperature, To is the baseline or starting temperature (the temperature at which the sensor was baselined), W is the temperature compensation factor, $P_n$ is the current pressure, $P_0$ is the baseline or starting pressure (the pressure at which the sensor was baselined), Z is the pressure compensation factor, $C_n$ is the current concentration of a gas (other than the at least one analyte of interest, such as a VOC) proximate the sensor, $C_0$ is a baseline concentration of the gas, and X is a gas compensation factor. If the sensor is compensated for more than one additional gas, Equation (2) may include additional terms for the compensation of each gas proximate the sensor. In one embodiment, the baseline resistance of the sensor is calibrated in a factory against the environmental factors (i.e., the baseline resistance of the sensor at given environmental conditions). For example, $R_{raw}$ may be established as a function of AH as illustrated in FIG. 3B (e.g., the sensitivity of the sensor to humidity) and $R_{comp}$ may be established with a mathematical function or a look-up table. In another embodiment, $R_{raw}$ may be established for a given AH, T, P, and gas concentration (i.e., $AH_0$, $T_0$, $P_0$, and $C_0$ in Equation (2)), and the current values of humidity, temperature, pressure, and gas concentration (i.e., $AH_n$, $T_n$, $P_n$, and $C_n$ in Equation (2)) are used in Equation (2) to compensate $R_{raw}$ and determine the value of $R_{comp}$. In this embodiment, the $R_{raw}$ is the raw sensor response or resistance value when the sensor is turned on, and the compensated resistance value, $R_{comp}$, is calculated continuously as a function of $R_{raw}$ and environmental conditions (e.g., $AH_n$, $T_n$, $P_n$, and $C_n$) at any given time using Equation (2). A complete expression of the calibrated and compensated gas concentration may be derived by substituting $R_{comp}$ from Equation (2) into Equation (1). In some embodiments, Q, W, Z, and X may correspond to embodiments where the sensitivity of the sensor to the respective one of the humidity, temperature, pressure, and gas concentration is not linear (e.g., as in FIG. 4A) and are factors that are derived from the respective sensitivities by, for example, performing empirical testing and using exponential curve fitting methods, or another method.

As another nonlimiting example, the compensated sensor response may be determined according to Equation (3) below:

$$\Delta R_{comp} = \Delta R + (CF_H * H + x) + (CF_T * T + y) + (CF_P * P + z) + (CF_C * C + w) \quad (3),$$

wherein $\Delta R_{comp}$ is the compensated sensor response, $\Delta R$ is the same as described above and corresponds to the change in one or more of resistance, resonant frequency, voltage, and current of gas sensor responsive to exposure to a sample relative to a respective baseline resistance, resonant frequency, voltage, or current of the sensor, $CF_H$ is the humidity compensation factor, H is the humidity (one of absolute humidity or relative humidity) proximate the sensor, $CF_T$ is the temperature compensation factor, T is the temperature proximate the sensor (e.g., in Kelvin, Celsius, or Fahrenheit), $CF_P$ is the pressure compensation factor, P is the pressure (e.g., absolute pressure) proximate the sensor, $CF_C$ is the concentration compensation factor, C is the concentration of a gas (other than the at least one analyte of interest) proximate the sensor, and each of w, x, y, and z are numeric constants. In some embodiments, the sensor may be compensated for more than one additional gas proximate the sensor by adding similar terms to Equation (3) for each additional gas. Although Equation (3) has been described with reference to a change in resistance, the disclosure is not so limited. In other embodiments, the compensated sensor response may correspond to changes in a resonant frequency of the sensor, changes in voltage of the sensor, or changes in current of the sensor. In some embodiments, $CF_H$, $CF_T$, $CF_P$, and $CF_C$ correspond to the sensitivity of the sensor to the respective one of humidity, temperature, pressure, and gas concentration proximate the sensor. In some such embodiments, the relationship between the response of the sensor and each of humidity, temperature, pressure, and gas concentration (e.g., the sensitivity of the sensor to each of humidity, temperature, pressure, and gas concentration) may be linear, as in FIG. 4A, for example.

Although Equation (3) is a particular equation for compensating the sensor output, the disclosure is not so limited and the raw sensor data may be compensated for one or more of humidity, temperature, pressure, and concentration of the one or more gases according to other equations using one or more of the respective humidity compensation factor, the temperature compensation factor, the pressure compensation factor, and gas concentration compensation factor. For example, each of the humidity compensation factor, the temperature compensation factor, the pressure compensation factor, and the gas concentration compensation factor may be a non-linear function related to the respective one of the humidity, temperature, pressure, and one or more other gases proximate the sensor. As will be described herein, in some embodiments, the compensation factors may be adjusted based on the sensitivity of the sensor to each of humidity, temperature, pressure, and concentration of the one or more gases, which may increase an accuracy of the sensor.

Act 108 includes determining a concentration of the at least one analyte of interest based on the compensated sensor output and the current calibration factors. The concentration of the at least one analyte of interest may be determined according to Equation (4) below:

$$C_{analyte}=(\Delta R_{comp}*S_0*S_{(H,T,P,C)}) \quad (4),$$

wherein $C_{analyte}$ is the concentration of the analyte gas of interest, $\Delta R_{comp}$ is the compensated sensor response (determined in act 106), $S_0$ is the current relationship between the sensitivity of the sensor to the at least one analyte of interest to the sensitivity of the sensor to the one or more of humidity, temperature, pressure, or concentration of the one or more gases (e.g., the initial relationship or an adjusted relationship based on the current sensitivities) of the sensor correlating at least one property of a sample (e.g., the concentration of the analyte of interest) to one of the response of the sensor or the change in the response of the sensor relative to a baseline sensor response of the sensor, and $S_{(H, T, P, C)}$ is the current sensitivity of the sensor to the one or more of humidity, temperature, pressure, and concentration of one or more gases (other than the at least one analyte of interest) proximate the sensor. In some embodiments, $S_0$ comprises the relationship between the sensitivity of the sensor to at least one analyte of interest to the sensitivity of the sensor to one or more of humidity, temperature, pressure, and gas concentration. As discussed above, the value of function $S_0$ may be determined with a look-up table, a mathematical correlation between the sensitivity of the gas sensor to one or more of humidity, temperature, pressure, and concentration of the one or more gases and the sensitivity of the gas sensor to the analyte, or another method (e.g., the slope of curve 202 or curve 204 of FIG. 2B at a particular time corresponding to the current sensitivity of the sensor to one or more of humidity, temperature, pressure, and concentration of the one or more gases). For example, $S_0$ may correspond to the slope of curve 202 or curve 204 at a particular time. In other embodiments, $S_0$ comprises a mathematical equation. In some embodiments, $S_0$ is determined in a factory, such as during act 102. In other embodiments, $S_0$ is the most recent calibration factor and as determined from, for example, FIG. 2B. In other words, $S_0$ is the relationship between the sensitivity of the sensor to the analyte of interest to the sensitivity of the sensor to the one or more of humidity, temperature, pressure, and the concentration of the one or more gases (i.e., $S_0=S_g/S_{(H, T, P, C)}$). Accordingly, multiplying the $S_0$ by $S_{(H, T, P, C)}$ results in the sensitivity of the sensor to the at least one analyte of interest (i.e., $S_g$). $\Delta R_{comp}$ of Equation (4) may be replaced with $R_{comp}$ determined from Equation (2), Equation (3), or any compensated sensor response for environmental conditions. As described above, the value of $S_0$ may be determined in a factory during initial calibration of the sensor, such as during act 102. As will be described herein, the value of $S_0$ may be adjusted based on the current sensitivity of the sensor to one or more of humidity, temperature, pressure, and concentration of the one or more gases proximate the sensor. In some embodiments, Equation (4) may be rewritten as Equation (5) below:

$$C_{analyte}=(\Delta R_{comp}*S_g) \quad (5),$$

wherein $S_g$ comprises a calibration factor and is determined based on the current sensitivity of the sensor to the one or more of humidity, temperature, pressure, and the one or more gases, as described above with reference to FIG. 2A and FIG. 2B.

Act 110 includes outputting at least one property of the gas sample (e.g., a concentration of the analyte of interest) and saving all data in a memory associated with the sensor. Results that do not exceed a predetermined gas concentration threshold are saved to the historical data file. In other words, determined concentrations (based on the compensated and calibrated response) that do not correspond to the presence of an analyte of interest may be saved to the historical data file in the memory. The historical data file is used to determine the sensitivity of the sensor to humidity (e.g., absolute humidity, relative humidity), temperature, pressure, and concentration of the one or more gases proximate the sensor. Data that exceeds the predetermined value, indicating the presence of a gas, may be saved to a separate data set in the memory. The data may include the compensated sensor response, the current calibration factors, the gas sample concentration, the raw data, temperature, pressure, relative humidity, concentration of one or more gases proximate the sensor, time information (e.g., date, time, duration of sensor operation, the time of sensor responses), etc., all of which may be stored in a memory associated with the sensor. The at least one property may include the concentration of the at least one analyte of interest, a thermal conductivity of the gas sample, a composition of the gas sample (e.g., a mole fraction of each component of the gas sample, a mole fraction of one or more components of the gas sample), or another property of the gas sample. In some embodiments, the data and the compensated sensor response data may be stored in the system memory.

With continued reference to FIG. 1, act 112 includes updating the compensation and calibration factors based on the historical data stored in the memory associated with the sensor. Act 112 includes determining the sensitivity of the sensor to temperature, pressure, humidity, and concentration of one or more gases (other than the at least one analyte of interest) proximate the sensor over a historical range (e.g., based on historical data, such as data obtained during acts 104 through 110). In some embodiments, the historical data does not contain data corresponding to a response of the sensor to exposure to a sample with an analyte gas present (e.g., when the compensated data exceeds the predetermined value (threshold)). Analysis of the historical data may include averaging the data (the sensor response) across a range of environmental conditions using hundreds, thousands, or more data samples. Outlying historical data values (which may be caused by noise or background gas concentrations that do not exceed the detection threshold) may be rejected to enhance the data "smoothing." The lack of analyte gas in the historical data can also be determined using other techniques. In one embodiment, determining the correlation of the response of the sensor in time to changes in humidity, temperature, pressure, or concentration of the one or more gases may be used to determine whether a current sensor response is due to the presence of an analyte. For example, if the sensor response always coincides with a change in humidity, temperature, pressure, or the concentration of the one or more gases, this is a strong indicator that humidity, temperature, or pressure is the source of the change in the response of the sensor. If some changes in humidity, temperature, pressure, or concentration of the one or more gases result in accurate compensation, and other changes in humidity, temperature, pressure, or the concentration of the one or more gases do not result in accurate compensation, the inaccurate compensation may be an indication that an additional gas was present at such times. As yet another example, in a multi-sensor system, if none of the sensors of the multi-sensor system indicate the presence of the at least one analyte of interest (another gas other than a baseline gas (e.g., air)), this would also be a good indication that an interfering gas is not present. In use and operation, the humidity, temperature, pressure, concentration of the one or more gases, and the sensor output (Soot) are measured. The sensor output may be compensated using sensitivity factors for humidity, temperature, pressure, and gas concentration ($S_H$, $S_T$, $S_P$, and $S_C$) to eliminate or reduce the effects of humidity, temperature, and pressure on the sensor output, as described above with reference to act 106, and Equation (2) and Equation (3), for example.

Act 112 further includes determining if the current compensation factors are adequate. If a residual compensation error (as shown in FIG. 5) exceeds a predetermined value (threshold) (e.g., if the $R_{comp}$ value deviates by more than about 5 percent from a baseline value), the compensation factors may be adjusted. By way of example, if the value of $R_{comp}$ exceeds the predetermined value (e.g., a humidity compensation error exceeds the predetermined value (threshold)), the humidity compensation factor may be adjusted based on the most recent historical data. In this example (referring to FIG. 5), since the sensitivity of the sensor to humidity changed, the sensitivity of the sensor to a gas or analyte of interest may exhibit a change based on the relationship between the sensitivity of the sensor to humidity and the sensitivity of the sensor to the gas or analyte of interest (e.g., as indicated in FIG. 2B, for example). Hence the calibration factor may be adjusted as indicated at act b) of act 112 according to the relationship established in act 102 and as illustrated in FIG. 2B.

In some embodiments, act 112 may include analyzing the historical data to determine the accuracy of the compensation and calibration factors. In some embodiments, the historical data collected when no analyte is present may be averaged to obtain a slope corresponding to the sensitivity of the sensor to each of humidity, temperature, pressure (as described above with reference to FIG. 4A), and concentration of the one or more gases. The determined slope may be used to adjust the compensation factors of the sensor for each of the respective humidity, temperature, pressure, and concentration of the one or more gases. Once the sensitivity of the sensor to humidity, temperature, pressure, and the one or more gases are determined, the sensitivity of the sensor to an analyte gas can be determined, as described above with reference to act 102 and FIG. 2A and FIG. 2B.

FIG. 3B illustrates a change in the sensitivity of the sensor to humidity over time. Such a change may indicate that the compensation and calibration factors may be adjusted in order to maintain the accuracy of the sensor. FIG. 3C illustrates a method of eliminating noise in the sensor response caused by trace amounts of gases or volatile organic compounds (VOCs) proximate the sensor. Any interfering gas may cause a downward excursion in the response of the sensor, and hence the accuracy may be improved by only using the most positive data points in the historical data. In other words, in some embodiments, one or both of act 104 and 106 may include correcting the output of the sensor for noise in the output of the sensor due to the presence of trace gases or volatile organic compounds, as indicated in FIG. 3C.

In some embodiments, the system may be configured to determine the accuracy of the compensation factors and the calibration factors after a predetermined duration, such as, for example, every second, every minute, every hour, every 6 hours, every 12 hours, every day, every 2 days, every 4 days, every week, every other week, every month, every predetermined number of months, etc. In other embodiments, the system may be configured to check the accuracy of the compensation factors and the calibration factors after a predetermined number of measurements have been made and stored by the gas sensor, such as, for example, after every measurement, after every about 10 measurements, after every about 50 measurements, after every about 100 measurements, after every about 250 measurements, after every about 500 measurements, after every about 1,000 measurements, or after every about 5,000 or more measurements. In some embodiments, the compensation and calibration factors may be adjusted based on the rate of change of the compensation values detected in the historical data. For example the error detected in the compensation values may not exceed the threshold value, but the change from one or more historical values to the subsequent historical values may indicate a trend that indicates the compensation values and calibration factors should be adjusted.

In some embodiments, determining the current sensitivity of the sensor to humidity, temperature, pressure, and concentration of one or more gases may include compensating the output signal of the sensor for one or more of humidity, temperature, pressure, and concentration of one or more gases as indicated in Equation (2), for example. In other embodiments, the output of the sensor may be compensated based on one or more known relationships between a change in the output of the sensor per change in the temperature to which the sensor is exposed (i.e., $\Delta R/\Delta T$, which may be referred to as the sensitivity of the sensor to temperature) and the change in the output of the sensor per change in concentration of humidity to which the sensor is exposed (i.e., $\Delta R/ppm\ H_2O$). For example, with reference to FIG. 4A, the relationship may be graphically represented for several discrete time intervals, $T_0$ being the initial sensor response and $T_3$ representing the most recent sensor response, typically after a long period of time has elapsed. Hence, the curves labeled $T_0$ through $T_3$ show how the sensor ages over time. Initially, in some embodiments, the relationship may be determined in a laboratory. In other words, the sensitivity of the sensor to the one or more of humidity, temperature, pressure, and concentration of one or more gases may be determined at various times as the sensor ages. In other embodiments, the relationship is based on known mathematical equations. In other embodiments, the curves may be accumulated from the sensors in use and operation in the field, such as through data obtained through the communications port 718 (FIG. 7). With reference to FIG. 4A, the output signal from the sensor may be compensated based on the sensitivity of the sensor to one or more of humidity, temperature, pressure, and concentration of one or more gases and the respective current humidity, temperature, pressure, and concentration of one or more gases. With reference to FIG. 4B, the output signal from the sensor when exposed to an analyte of interest may also vary from the initial sensor response ($T_0$) to the most recent sensor response ($T_3$) as the sensor ages. In other words, the sensitivity of the sensor to an analyte of interest (FIG. 4B) may be adjusted by the response of the sensor to humidity, temperature, pressure, or concentration of one or more gases (FIG. 4A) by multiplying the sensitivity of the sensor to humidity, temperature, pressure, or concentration of the one or more VOCs by a factor as defined by the ratio of the sensitivity to the sensor to the at least one analyte gas to the sensitivity of the sensor to absolute temperature, pressure, humidity, or concentration of the one or more gases as shown in FIG. 2B as a function of time. As described above, in other embodiments, the sensitivity of the sensor to the analyte of interest may be adjusted based on a look-up table or a mathematical correlation between the sensitivity of the sensor to the analyte of interest and the sensitivity of the sensor to one or more of humidity, temperature, pressure, and concentration of the one or more gases.

In some embodiments, the calibration factor $S_0$ may be adjusted based on the current sensitivity of the sensor to humidity, temperature, pressure, or concentration of one or more gases and the relationship between the sensitivity of the sensor to humidity, temperature, pressure, or concentration of one or more gases and the sensitivity of the sensor to the analyte of interest determined in act 102 and shown in FIG. 2B. Accordingly, the current sensitivity of the sensor to humidity, temperature, pressure, or concentration of one or more gases may be used to determine the current sensitivity of the sensor to the at least one analyte of interest based on the predetermined relationship between the sensitivity of the sensor to humidity, temperature, pressure, or concentration of one or more VOCs and the sensitivity of the sensor to the analyte of interest.

Accordingly, an adjusted calibration factor may be determined periodically based on the current sensitivity of the sensor to exposure to the analyte of interest, which may be determined based on the current sensitivity of the gas sensor to exposure to temperature, pressure, or humidity.

In some embodiments, after the compensation factors and the calibration factor are updated, the method 100 includes returning to act 104 and repeating acts 104 through 112.

Although FIG. 1 has been described as including a particular order, the disclosure is not so limited. In other embodiments, the method 100 may proceed in any order and other than the particular order shown in FIG. 1.

Although the adjusted calibration factor has been described as being used for determining a concentration of the analyte of interest, in other embodiments, the adjusted calibration factor may be used for determining another property or condition of a sample to which the sensor is exposed. In some such embodiments, the adjusted calibration factor may be used to adjust an output signal of the sensor, which adjusted output signal may be used to determine at least one property of the sample such as the type of gas present (e.g., identify of various gases, composition of the gas sample).

Accordingly, a method of determining at least one property of a gas sample including at least one analyte of interest includes determining typical sensor performance (e.g., factory characterization) of a sensor. For example, determining the typical sensor performance may include determining the sensitivity of the sensor to one or more of humidity (e.g., absolute humidity, relative humidity), temperature, pressure, and concentration of one or more gases (other than the at least one analyte of interest) over a period of time (e.g., days, weeks, months, annually, etc.), as described above with reference to act 102 and FIG. 4A, determining the change in the sensor sensitivity to at least one analyte of interest over the same period of time, as described above with reference to act 102 and FIB. 4B, determining the relationship between the change in the sensitivity of the sensor to one or more of humidity, temperature, pressure, and concentration of one or more gases to the change in sensitivity of the sensor to the at least one analyte of interest, as described above with reference to act 102 and FIG. 1, and determining and saving initial compensation factors and calibration factors. The method further includes deploying the sensor, collecting, storing, and reporting data obtained with the sensor. For example, raw data may be collected from an environmental sensor (including temperature, pressure, humidity (e.g., absolute humidity, relative humidity), and concentration of one or more gases data) and data may be collected from the sensor (e.g., the response of the sensor). The sensor response may be compensated with currently stored compensation factors and the compensated sensor response may be calibrated based on current calibration factors. The method further includes updating the compensation and calibration factors after sufficient historical data has been collected. For example, the current sensitivity of the sensor to absolute humidity may be determined using historical data, as described above with reference to act 112 and FIG. 3B. The method includes determining if the compensation factors are adequately removing the effects of temperature, pressure, and absolute humidity using the historical data, as described above with reference to act 112 and FIG. 5 (described below). In addition, the relationship between the sensitivity of the sensor to absolute humidity and the sensitivity of the sensor to the at least one analyte (determined during act 102) may be used to update the calibration factor based on the current sensitivity of the sensor to humidity (e.g., absolute humidity), temperature, pressure, and the one or more gases.

In some embodiments, the functionality of the sensor (e.g., whether the sensor is operational) may be determined based, at least in part, on the relationship between the sensitivity of the sensor to humidity and the humidity proximate the sensor. The humidity proximate the sensor may be measured and determined as described above, such as with an environmental humidity sensor or with a hotplate sensor.

For example, the relationship between the humidity proximate a gas sensor and the sensitivity of the gas sensor to humidity may be used to determine the whether the gas sensor is operating as intended (e.g., whether the gas sensor is exposed to the humidity proximate the gas sensor). For example, the relationship between the humidity and the response of the gas sensor (e.g., the sensitivity of the sensor to humidity) may be used to determine whether the gas sensor is exposed to the sample including the humidity. In other words, the gas sensor may exhibit a response based on the humidity level proximate the gas sensor, which humidity level is measured by the humidity sensor. In some embodiments, such as where the gas sensor does not exhibit a response that correlates to the humidity measured by the humidity sensor, it may be determined that the gas sensor is not sufficiently exposed to the surrounding atmosphere, indicating that the gas sensor is unsuitable for use and not operating properly. Responsive to determining that the response of the gas sensor does not match the measured humidity, the gas sensor may be configured to provide an indication that the gas sensor has failed.

In some such embodiments, the humidity measured by the sensor may be used to self-check the sensor for proper operation (e.g., to determine whether the sensor is plugged and sufficiently exposed to gases in a surrounding environment). In some embodiments, the diurnal variations in humidity that the gas sensor is exposed to may be used to facilitate a so-called "bump test" and determine whether the gas sensor is functional. In other words, the humidity to which the gas sensor is exposed may be measured with the humidity sensor and the response of the gas sensor may be checked against the measured humidity level to determine whether the response of the gas sensor matches the expected response of the gas sensor based on the measured humidity level.

In some embodiments, characteristic responses of the sensor or the response behavior, or the response behavior of the sensor with respect to humidity, temperature, and pressure may be monitored for evidence that the sensor is not exposed to the surrounding environment. For example, the sensor may include a processing subsystem to determine that the sensor is not exposed to the surrounding environment responsive to measuring one or more of the humidity, temperature, and pressure over a duration without fluctuations in the one or more of the humidity, temperature, and pressure or with fluctuations in the one or more of humidity, temperature, and pressure that are substantially damped compared to historical fluctuations over a corresponding duration (e.g., hours, a day, etc.). The indication that the one or more of humidity, temperature, and pressure do not exhibit fluctuations or damped fluctuations over the duration may be an indication of a blockage in the sensor such that environmental gases (e.g., air, including humidity) are not freely flowing into or out of the sensor. In some embodiments, the sensor includes a processing subsystem configured to machine learn, or including artificial intelligence algorithms to recognize a pattern of the sensor outputs over a duration and environmental sensor outputs over the same duration to determine when the output of the sensor does not match that of historical outputs, indicating a change in the ingress and/or egress of ambient environmental gases (e.g., air).

The sensor may comprise any type of sensor configured for measuring at least one property (e.g., a flow, a presence, an identity, a composition, a concentration of one or more components) of at least one analyte of interest. In some embodiments, the sensor is configured to determine a presence of at least one analyte of interest and may further be configured to determine a concentration of the at least one analyte of interest. By way of nonlimiting example, the sensor may comprise a metal oxide semiconductor (MOS) sensor, an electrochemical sensor, a resonant sensor (e.g., a microcantilever sensor), a catalytic sensor, a thermal conductivity sensor, a polymer sensor, an optical sensor, or another sensor.

Figure 6A:
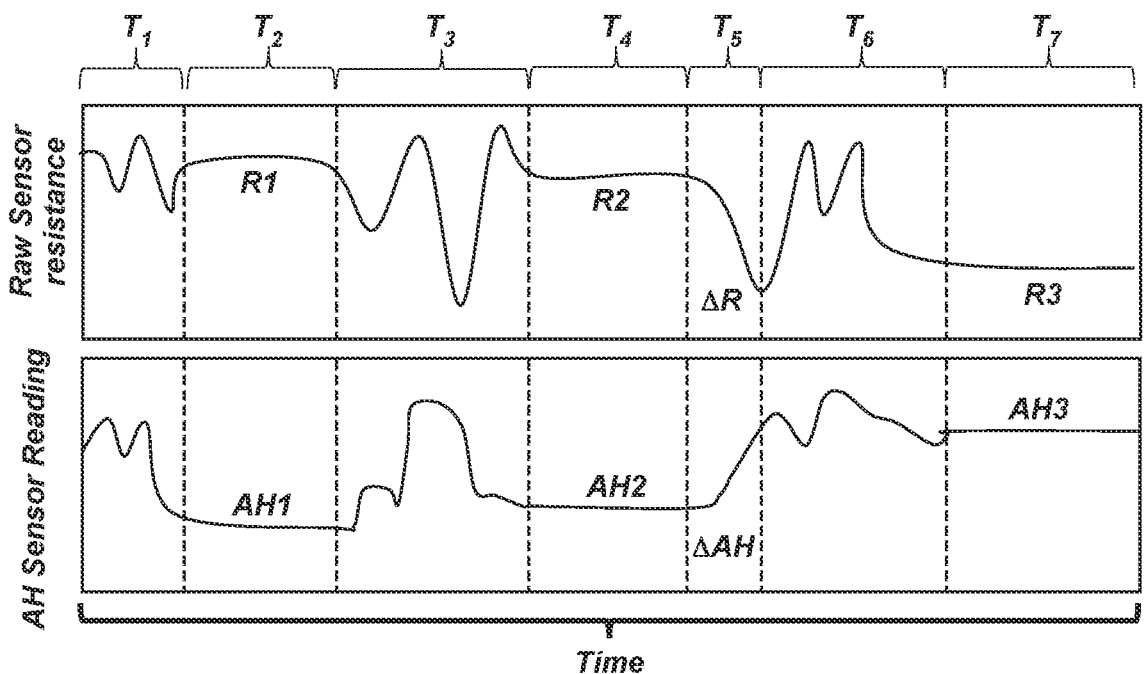
FIG. 6A illustrates the sensor resistance over a period of time along with corresponding absolute humidity changes, in accordance with embodiments of the disclosure.
Figure 6B:
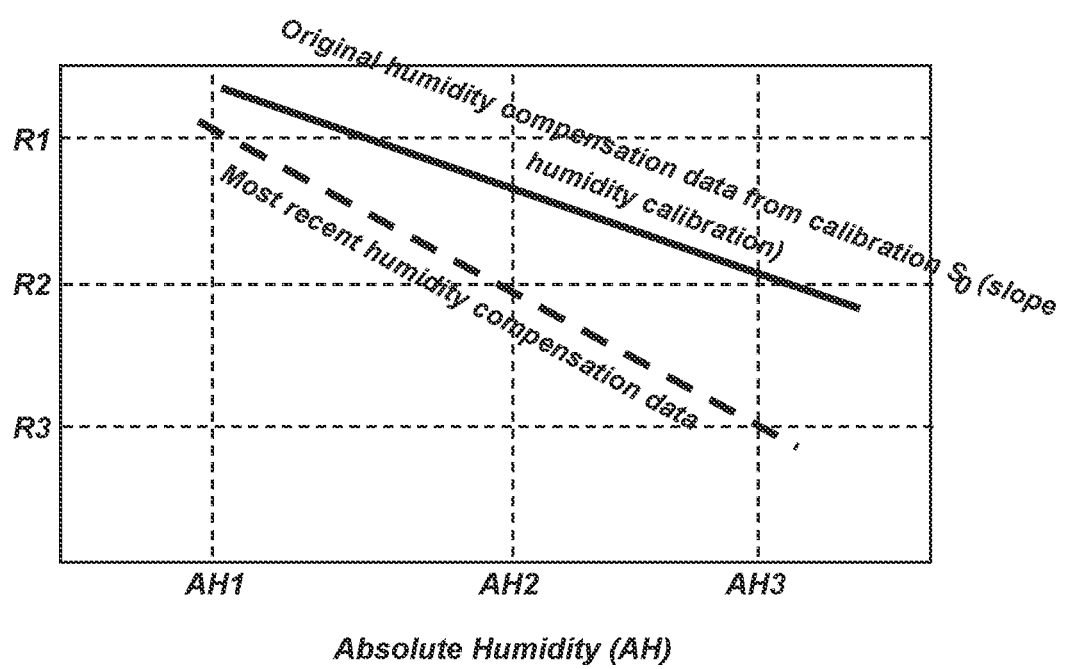
FIG. 6B illustrates the sensor resistance plotted against absolute humidity taken from FIG. 6A, in accordance with embodiments of the disclosure.

FIG. 6A illustrates how the raw sensor response might respond over a 3-day period with respect to absolute humidity changes. The sensor response and absolute humidity response (the response of an absolute humidity sensor) are measured concurrently. FIG. 6A illustrates different time periods ($T_1$, $T_2$, $T_3$, $T_4$, $T_5$, $T_6$, and $T_7$) during which different events occur. During $T_1$, $T_3$, and $T_6$, a concentration of volatile organic compounds (VOCs) proximate the gas sensor are changing and the sensor exhibits a varying response. During $T_2$, $T_4$, and $T_7$, there are no substantial changes in the gas proximate the gas sensor or in the absolute humidity proximate the gas sensor. During $T_5$, the humidity proximate the gas sensor changes while there is no substantial change in the VOCs concentration (or the analyte of interest) proximate the gas sensor. During $T_2$, $T_4$, and $T_7$ the response of the gas sensor is represented as R1, R2, and R3, respectively and the response of the absolute humidity sensor is AH1, AH2, and AH3, respectively. In some embodiments, humidity versus sensor response data may be collected during these flat regions. FIG. 6B illustrates the sensor response as a function of the absolute humidity proximate the gas sensor. Data illustrated in FIG. 6B may be collected during the periods of R1, R2, and R3 of FIG. 6A, since no analyte gases are present during these time periods. As illustrated in FIG. 6B, the sensitivity of the gas sensor may change with time relative to the initial sensitivity of the gas sensor. Alternately, another time period ($T_5$) is shown in FIG. 6A, wherein the sensor response is labeled ΔR and the absolute humidity response is labeled ΔAH, the absolute humidity is changing relatively rapidly, and the raw sensor data is tracking the absolute humidity change. In some embodiments, humidity versus sensor response data may be collected during this period to determine the current sensitivity of the gas sensor to humidity.

FIG. 7 is a simplified block diagram of a detector 700 including one or more sensors (e.g., gas sensors), in accordance with embodiments of the disclosure. The detector 700 includes a housing 702 housing one or more sensors, such as at least one gas sensor 704 and at least one environmental sensor 706 to detect temperature, pressure and/or humidity. The gas sensor 704 may include one or more of the gas sensors described herein and configured to determine at least one property of a sample based, at least in part, on a relationship between a sensitivity of the gas sensor 704 to temperature, pressure or humidity and a sensitivity of the gas sensor 704 to exposure to the analyte of interest. In some embodiments, each of the gas sensor 704 and the environmental sensor 706 are disposed on the same substrate.

A processing subsystem 720 (also referred to herein as a "subsystem") may be interfaced to analog to digital (A/D) and digital to analog (D/A) converters 708 though a data bus 712 to the individual sensors 704, 706. The processing subsystem 720 may include a processor 714, such as a central processing unit (CPU), a memory 716 (including software, databases, baseline data, calibration data, etc.), a communications port 718, and optionally a graphical user interface (GUI) 710 in operable communication with the central processing unit 714. The communications port 718 may be in operable communication with one or more devices 722, such as one or more input devices and one or more output devices. The communications port 718 may also be used to update firmware or software when the sensors are deployed in the field. In some embodiments, flame arrestors and filters may be used between some or all of the sensors 704, 706 and the gas sample being analyzed.

In use and operation, the detector 700 may be configured to continuously expose the gas sensor 704 and the environmental sensor 706 to a sample representative of the atmosphere proximate the detector 700. An output from the environmental sensor 706 may be transmitted to the processor 714, which may communicate with the memory 716 and determine a humidity concentration proximate the detector 700. The processor 714 and the memory 716 may be configured to determine a current sensitivity of the gas sensor 704 to exposure to humidity based on the output of the gas sensor 704 at various humidity concentrations to which the gas sensor 704 is exposed during normal operation of the detector 700. The current sensitivity of the gas sensor 704 to humidity may be used to recalibrate the gas sensor 704 based on a correlation between the sensitivity of the gas sensor 704 to humidity and a sensitivity of the gas sensor 704 to the analyte of interest. In some embodiments, the processor 714 is configured to recalibrate the gas sensor 704 periodically (e.g., seconds, minutes, hours, every four hours, every six hours, every twelve hours, every day, every week, etc.). In yet other embodiments, the processor 714 is configured to recalibrate the gas sensor 704 after determining that there is a compensation error. Accordingly, the detector 700 may be configured to continuously recalibrate the gas sensor 704 in real time as the detector 700 and gas sensor 704 age.

In some embodiments, as the sensor ages, a change in resistance of the sensor responsive to exposure to a same concentration of the analyte of interest may decrease. In other words, the response (e.g., the signal) of the sensor to exposure to the same concentration of the analyte of interest may decrease as the sensor ages. According to the embodiments described herein, a detector may use water vapor concentration (e.g., humidity), temperature, and/or pressure data obtained during natural variations (e.g., diurnal variations) in such conditions in the atmosphere to determine the current sensitivity of the sensor to exposure to humidity, temperature, and/or pressure. The sensitivity of the sensor to humidity, temperature, and/or pressure may be proportional to the sensitivity of the sensor to one or more analyses of interest. Accordingly, the sensor may be periodically calibrated while remaining in service without the use of a separate calibration gas or for calibrating the sensor. In other words, in some embodiments, the sensor may be calibrated with humidity, a vapor to which the gas sensor is exposed during normal use and operation or to which it could be intentionally exposed, for instance during factory calibration. Since the detector may be located in an environment exhibiting sinusoidal variations in humidity concentration, the sensor associated with the detector may naturally be exposed to different humidity concentrations, which may facilitate determination of the sensitivity of the sensor to exposure to humidity. In other words, the data used for determining the current sensitivity of the sensor to humidity may be naturally present proximate the sensor.

Additional nonlimiting example embodiments of the disclosure are set forth below.

Embodiment 1: A method of calibrating a gas sensor, the method comprising: determining a sensitivity of a gas sensor to one or more conditions proximate the gas sensor; determining one or more initial calibration factors comprising a sensitivity of the gas sensor to one or more analytes of interest; determining a current sensitivity of the gas sensor to the one or more conditions proximate the gas sensor by measuring a response of the gas sensor while the one or more conditions proximate the gas sensor varies during operation of the gas sensor; and adjusting the one or more initial calibration factors of the gas sensor based, at least in part, on: the current sensitivity of the gas sensor to the one or more conditions proximate the gas sensor; and a relationship between the sensitivity of the gas sensor to the one or more analytes of interest to the sensitivity of the gas sensor to the one or more conditions proximate the gas sensor.

Embodiment 2: The method of Embodiment 1, wherein determining a sensitivity of a gas sensor to one or more conditions proximate the gas sensor comprises determining a sensitivity of the gas sensor to one or more of humidity, temperature, pressure, and concertation of one or more volatile organic compounds proximate the gas sensor.

Embodiment 3: The method of Embodiment 1 or Embodiment 2, wherein determining a current sensitivity of the gas sensor to the one or more conditions proximate the gas sensor comprises determining the current sensitivity of the gas sensor to the one or more conditions at predetermined time intervals.

Embodiment 4: The method of any one of Embodiments 1 through 3, further comprising determining the relationship between the sensitivity of the gas sensor to the one or more conditions proximate the gas sensor in a laboratory.

Embodiment 5: The method of Embodiment 4, wherein determining the relationship between the sensitivity of the gas sensor to the one or more conditions proximate the gas sensor in a laboratory comprises periodically updating the gas sensor while the gas sensor is in use via a communications channel contained in a sensor assembly associated with the gas sensor.

Embodiment 6: The method of any one of Embodiments 1 through 5, further comprising adjusting the one or more initial calibration factors based on a total dosage of gases to which the gas sensor is exposed.

Embodiment 7: The method of any one of Embodiments 1 through 6, wherein adjusting the one or more initial calibration factors comprises adjusting the calibration factor based on a rate of change of the sensitivity of the gas sensor to the one or more conditions proximate the gas sensor to the sensitivity of the gas sensor to one or more analytes of interest.

Embodiment 8: The method of any one of Embodiments 1 through 7, further consisting of selecting the gas sensor to comprise at least one of a metal oxide semiconductor sensor, a resonant sensor, an electrochemical sensor, a catalytic sensor, a thermal conductivity sensor, or an optical sensor.

Embodiment 9: The method of any one of Embodiments 1 through 8, further comprising: compensating an output of the gas sensor for effects of humidity, temperature, pressure, and gas concentration proximate the gas sensor to determine a compensated sensor output; and adjusting the compensated sensor output based on the adjusted one or more initial calibration factor.

Embodiment 10: The method of any one of Embodiments 1 through 9, wherein determining a current sensitivity of the gas sensor to the one or more conditions proximate the gas sensor comprises determining the current sensitivity of the gas sensor to the one or more conditions proximate the gas sensor with one or more of a humidity sensor, a temperature sensor, a pressure sensor, and a volatile organic compound sensor integrated with the gas sensor.

Embodiment 11: The method of any one of Embodiments 1 through 10, wherein the gas sensor comprises a hotplate, further comprising determining a temperature and a humidity with the hotplate.

Embodiment 12: The method of any one of Embodiments 1 through 11, wherein the gas sensor comprises a thermal conductivity sensor, further comprising determining one or more of humidity, temperature, and pressure with the thermal conductivity sensor.

Embodiment 13: The method of any one of Embodiments 1 through 12, further comprising determining a pressure with a diaphragm.

Embodiment 14: The method of any one of Embodiments 1 through 13, further comprising determining a pressure or humidity with one or more resonant sensors.

Embodiment 15: A method of operating a gas sensor configured to detect at least one analyte of interest, the method comprising: determining at least one of a humidity compensation factor, a temperature compensation factor, and a pressure compensation factor by measuring a response of the sensor at one or more of a plurality of humidity levels, a plurality of temperatures, and a plurality of pressures in the absence of at least one analyte of interest; compensating a response of the gas sensor for effects of one or more of humidity, temperature, and pressure based on the at least one of the humidity compensation factor, the temperature compensation factor, and the pressure compensation factor and a current one or more of the humidity, temperature, and pressure proximate the sensor to determine a compensated response of the gas sensor; and calibrating the compensated response of the gas sensor based, at least in part, on a relationship between a sensitivity of the gas sensor to the at least one analyte of interest and a sensitivity of the gas sensor to the one or more of humidity, temperature, and pressure.

Embodiment 16: The method of Embodiment 15, further comprising adjusting the at least one of the humidity compensation factor, the temperature compensation factor, and the pressure compensation factor based on a current sensitivity of the gas sensor to the one or more of humidity, temperature, and pressure.

Embodiment 17: The method of Embodiment 15 or Embodiment 16, further comprising correlating changes in the response of the gas sensor to a change in the one or more of humidity, temperature, and pressure to determine the absence of the at least one analyte of interest.

Embodiment 18: The method of any one of Embodiments 15 through 17, further comprising determining the absence of the at least one analyte of interest based on a lack of a response from a plurality of additional gas sensors.

Embodiment 19: The method of any one of Embodiments 15 through 18, further comprising adjusting the at least one of the humidity compensation factor, the temperature compensation factor, and the pressure compensation factor based on historical sensor responses.

Embodiment 20: The method of any one of Embodiments 15 through 19, further comprising adjusting the at least one of the humidity compensation factor, the temperature compensation factor, and the pressure compensation factor responsive to determining the compensated response of the gas sensor greater than a predetermined amount in the absence of the at least one analyte of interest.

Embodiment 21: A method of operating a gas sensor to determine at least one property of a gas, the method comprising: measuring a response of a gas sensor to changes in humidity, temperature, and pressure and determining a sensitivity of the gas sensor to humidity, temperature, and pressure; and calibrating the response of the gas sensor when the gas sensor is exposed to at least one analyte of interest based, at least in part, on a relationship between the sensitivity of the gas sensor to the at least one analyte of interest and the sensitivity of the gas sensor to humidity, temperature, and pressure.

Embodiment 22: The method of Embodiment 21, further comprising determining at least one of a humidity compensation factor, a temperature compensation factor, and a pressure compensation factor based on a current sensitivity of the gas sensor to humidity, temperature, and pressure.

Embodiment 23: The method of Embodiment 21 or Embodiment 22, further comprising compensating the response of the gas sensor with at least one of a temperature compensation factor, a pressure compensation factor, or a humidity compensation factor to determine a compensated response of the gas sensor prior to calibrating the response of the gas sensor.

Embodiment 24: The method of Embodiment 23, wherein calibrating the response of the gas sensor comprises applying a mathematical function to the compensated response of the gas sensor, the mathematical function including a calibration factor based on the relationship between the sensitivity of the gas sensor to the at least one analyte of interest to the sensitivity and the gas sensor to humidity, temperature, and pressure.

Embodiment 25: The method of Embodiment 24, further comprising periodically adjusting the at least one of the temperature compensation factor, the pressure compensation factor, or the humidity compensation factor based on elapsed time, a quantity of historical data, a compensation error greater than a threshold value, or a rate of change of the at least one temperature compensation factor, the pressure compensation factor, or the humidity compensation factor.

Embodiment 26: A gas detector, comprising: a gas sensor configured to be exposed to one or more gases located proximate the gas sensor; at least one environmental sensor configured to determine at least one of humidity, temperature, and pressure proximate the gas sensor; and a processing subsystem configured to: determine a sensitivity of the gas sensor to one or more conditions proximate the gas sensor based on a relationship between an output of the gas sensor and the one or more conditions proximate the gas sensor; and calibrate the output of the gas sensor based on a relationship between the sensitivity of the gas sensor to the one or more conditions proximate the gas sensor and a sensitivity of the gas sensor to exposure to one or more gases of interest.

Embodiment 27: The gas detector of Embodiment 26, wherein the processing subsystem is further configured to compensate the output of the gas sensor for at least one of temperature, pressure, or humidity based on at least one of a temperature compensation factor, a pressure compensation factor, or a humidity compensation factor.

Embodiment 28: The gas detector of Embodiment 27, wherein the at least one of the temperature compensation factor, the pressure compensation factor, and the humidity compensation factor are adjusted over time based on environmental changes in at least one of humidity, temperature, and pressure proximate the gas sensor.

Embodiment 29: A method of determining a functionality of a gas sensor, the method comprising: measuring a condition proximate a gas sensor with a sensor while measuring a response of the gas sensor; and based on and the measured condition proximate the gas sensor and a response of the gas sensor at varying conditions proximate the gas sensor, determining a functionality of the gas sensor.

Embodiment 30: The method of Embodiment 29, wherein measuring a condition proximate a gas sensor with a sensor comprises measuring a humidity proximate the gas sensor with a humidity sensor.

Embodiment 31: The method of Embodiment 29 or Embodiment 30, further comprising: determining a sensitivity of the gas sensor to the condition; correlating the sensitivity of the gas sensor to the condition; and determining a blockage in the gas sensor responsive to changes in the measured condition that do not correspond in time with changes in the response of the gas sensor.

Embodiment 32: The method of any one of Embodiments 29 through 31, wherein determining a functionality of the gas sensor comprises determining a blockage in the gas sensor responsive to responses of the gas sensor that do not correlate in time to the measured condition proximate the gas sensor.

Embodiment 33: The method of any one of Embodiments 29 through 32, wherein: measuring a condition proximate the gas sensor comprises measuring diurnal variations in one or more of humidity, temperature, and pressure proximate the gas sensor; and determining a functionality of the gas sensor comprises determining a blockage in the gas sensor responsive to determining that the response of the gas sensor does not exhibit variations corresponding to the diurnal variations in the one or more of humidity, temperature, and pressure proximate the gas sensor.

While the disclosure is susceptible to various modifications and alternative forms, specific embodiments have been shown by way of example in the drawings and have been described in detail herein. However, the disclosure is not intended to be limited to the particular forms disclosed. Rather, the disclosure is to cover all modifications, equivalents, and alternatives falling within the scope of the disclosure as defined by the following accompanying claims and their legal equivalents.

What is claimed is:

1. A method of calibrating a gas sensor, the method comprising:
   determining an initial sensitivity of a gas sensor to one or more conditions proximate the gas sensor, the initial sensitivity comprising a relationship between an output of the gas sensor and the one or more conditions proximate the gas sensor;
   determining one or more calibration factors comprising a sensitivity of the gas sensor to one or more analytes of interest;
   after determining the initial sensitivity of the gas sensor to the one or more conditions proximate the gas sensor and determining the one or more calibration factors, determining a current sensitivity of the gas sensor to the one or more conditions proximate the gas sensor by measuring a response of the gas sensor while the one or more conditions proximate the gas sensor varies during operation of the gas sensor; and
   responsive to changes in the current sensitivity of the gas sensor to the one or more conditions proximate the gas sensor, adjusting the one or more calibration factors of the gas sensor to recalibrate the gas sensor over a lifetime of the gas sensor based, at least in part, on:
      the current sensitivity of the gas sensor to the one or more conditions proximate the gas sensor; and
      a relationship between the sensitivity of the gas sensor to the one or more analytes of interest to the sensitivity of the gas sensor and the one or more conditions proximate the gas sensor.

2. The method of claim 1, wherein determining an initial sensitivity of a gas sensor to one or more conditions proximate the gas sensor comprises determining a sensitivity of the gas sensor to one or more of humidity, temperature, pressure, and concertation of one or more volatile organic compounds proximate the gas sensor.

3. The method of claim 1, wherein determining a current sensitivity of the gas sensor to the one or more conditions proximate the gas sensor comprises determining the current sensitivity of the gas sensor to the one or more conditions at predetermined time intervals.

4. The method of claim 1, further comprising determining the relationship between the sensitivity of the gas sensor to the one or more analytes of interest and the sensitivity of the gas sensor to the one or more conditions proximate the gas sensor in a laboratory.

5. The method of claim 4, wherein determining the relationship between the sensitivity of the gas sensor to the one or more analytes of interest and the sensitivity of the gas sensor to the one or more conditions proximate the gas sensor in a laboratory comprises periodically updating the gas sensor while the gas sensor is in use via a communications channel contained in a sensor assembly associated with the gas sensor.

6. The method of claim 1, further comprising adjusting the one or more calibration factors based on a total dosage of gases to which the gas sensor is exposed.

7. The method of claim 1, wherein adjusting the one or more calibration factors comprises adjusting the one or more initial calibration factors based on a rate of change of the sensitivity of the gas sensor to the one or more conditions proximate the gas sensor to the sensitivity of the gas sensor to the one or more analytes of interest.

8. The method of claim 1, further comprising selecting the gas sensor to comprise at least one of a metal oxide semiconductor sensor, a resonant sensor, an electrochemical sensor, a catalytic sensor, a thermal conductivity sensor, or an optical sensor.

9. The method of claim 1, further comprising:
   compensating an output of the gas sensor for effects of humidity, temperature, pressure, and gas concentration proximate the gas sensor to determine a compensated sensor output; and
   adjusting the compensated sensor output based on the adjusted one or more initial calibration factors.

10. The method of claim 1, wherein determining a current sensitivity of the gas sensor to the one or more conditions proximate the gas sensor comprises determining the current sensitivity of the gas sensor to the one or more conditions proximate the gas sensor with one or more of a humidity sensor, a temperature sensor, a pressure sensor, and a volatile organic compound sensor integrated with the gas sensor.

11. The method of claim 1, wherein the gas sensor comprises a hotplate, further comprising determining a temperature and a humidity with the hotplate.

12. The method of claim 1, wherein the gas sensor comprises a thermal conductivity sensor, further comprising determining one or more of humidity, temperature, and pressure with the thermal conductivity sensor.

13. The method of claim 1, further comprising determining a pressure with a diaphragm.

14. The method of claim 1, further comprising determining a pressure or humidity with one or more resonant sensors.

15. The method of claim 1, further comprising determining whether the gas sensor is operational based, at least in part, on a relationship between a sensitivity of the gas sensor to humidity and a humidity proximate the gas sensor.

16. The method of claim 1, further comprising determining that the gas sensor is plugged based on a measured humidity proximate the gas sensor.

17. A gas detector, comprising:
   a gas sensor configured to be exposed to one or more gases located proximate the gas sensor;

at least one environmental sensor configured to determine at least one of humidity, temperature, and pressure proximate the gas sensor; and a processing subsystem configured to:
determine an initial sensitivity of the gas sensor to one or more conditions proximate the gas sensor, the initial sensitivity comprising a relationship between an output of the gas sensor and the one or more conditions proximate the gas sensor;

determine one or more calibration factors comprising a sensitivity of the gas sensor to one or more analytes of interest;

after determining the initial sensitivity of the gas sensor to the one or more conditions proximate the gas sensor and determining the one or more calibration factors, determining a current sensitivity of the gas sensor to the one or more conditions proximate the gas sensor by measuring a response of the gas sensor while the one or more conditions proximate the gas sensor varies during operation of the gas sensor; and responsive to changes in the current sensitivity of the gas sensor to the one or more conditions proximate the gas sensor, adjusting the one or more calibration factors of the gas sensor to recalibrate the gas sensor over a lifetime of the gas sensor based, at least in part, on:

the current sensitivity of the gas sensor to the one or more conditions proximate the gas sensor; and a relationship between the sensitivity of the gas sensor to the one or more analytes of interest to the sensitivity of the gas sensor and the one or more conditions proximate the gas sensor.

18. The gas detector of claim 17, wherein the processing subsystem is further configured to compensate the output of the gas sensor for at least one of temperature, pressure, or humidity based on at least one of a temperature compensation factor, a pressure compensation factor, or a humidity compensation factor.

19. The gas detector of claim 18, wherein the at least one of the temperature compensation factor, the pressure compensation factor, and the humidity compensation factor are adjusted over time based on environmental changes in at least one of humidity, temperature, and pressure proximate the gas sensor.

* * * * *